(12) United States Patent
Zhao

(10) Patent No.: US 7,553,836 B2
(45) Date of Patent: Jun. 30, 2009

(54) MELANIN CONCENTRATING HORMONE RECEPTOR-1 ANTAGONISTS

(75) Inventor: Guohua Zhao, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 59 days.

(21) Appl. No.: 11/671,150

(22) Filed: Feb. 5, 2007

(65) Prior Publication Data
US 2007/0185097 A1 Aug. 9, 2007

Related U.S. Application Data

(60) Provisional application No. 60/765,530, filed on Feb. 6, 2006.

(51) Int. Cl.
| | |
|---|---|
| A61K 31/4025 | (2006.01) |
| A61K 31/407 | (2006.01) |
| A61K 31/4985 | (2006.01) |
| C07D 487/04 | (2006.01) |
| C07D 207/00 | (2006.01) |

(52) U.S. Cl. .................. 514/249; 514/413; 514/422; 544/349; 548/453; 548/466; 548/518

(58) Field of Classification Search ................ 514/413, 514/249, 422; 544/349; 548/453, 518
See application file for complete search history.

(56) References Cited

U.S. PATENT DOCUMENTS

| | | | |
|---|---|---|---|
| 3,674,836 A | 7/1972 | Creger | |
| 3,983,140 A | 9/1976 | Endo et al. | |
| 4,027,009 A | 5/1977 | Grier et al. | |
| 4,231,938 A | 11/1980 | Monaghan et al. | |
| 4,346,227 A | 8/1982 | Terahara et al. | |
| 4,379,785 A | 4/1983 | Weyer et al. | |
| 4,448,784 A | 5/1984 | Glamkowski et al. | |
| 4,450,171 A | 5/1984 | Hoffman et al. | |
| 4,499,289 A | 2/1985 | Baran et al. | |
| 4,613,610 A | 9/1986 | Wareing | |
| 4,639,436 A | 1/1987 | Junge et al. | |
| 4,647,576 A | 3/1987 | Hoefle et al. | |
| 4,681,893 A | 7/1987 | Roth | |
| 4,686,237 A | 8/1987 | Anderson | |
| 4,759,923 A | 7/1988 | Buntin et al. | |
| 4,871,721 A | 10/1989 | Biller | |
| 4,904,769 A | 2/1990 | Rauenbusch | |
| 4,924,024 A | 5/1990 | Biller | |
| 5,006,530 A | 4/1991 | Angerbauer et al. | |
| 5,011,930 A | 4/1991 | Fujikawa et al. | |
| 5,177,080 A | 1/1993 | Angerbauer et al. | |
| 5,260,440 A | 11/1993 | Hirai et al. | |
| 5,273,995 A | 12/1993 | Roth | |
| 5,354,772 A | 10/1994 | Kathawala | |
| 5,385,929 A | 1/1995 | Bjorge et al. | |
| 5,434,150 A | 7/1995 | Austel et al. | |
| 5,447,954 A | 9/1995 | Gribble et al. | |
| 5,488,064 A | 1/1996 | Sher | |
| 5,491,134 A | 2/1996 | Sher et al. | |
| 5,506,219 A | 4/1996 | Robl | |
| 5,541,204 A | 7/1996 | Sher et al. | |
| 5,594,016 A | 1/1997 | Ueno et al. | |
| 5,612,359 A | 3/1997 | Murugesan | |
| 5,686,104 A | 11/1997 | Mills et al. | |
| 5,691,322 A | 11/1997 | Robl | |
| 5,698,527 A | 12/1997 | Kim | |
| 5,712,396 A | 1/1998 | Magnin et al. | |
| 5,753,675 A | 5/1998 | Wattanasin | |
| 5,770,615 A | 6/1998 | Cheng et al. | |
| 5,776,983 A | 7/1998 | Washburn et al. | |
| 5,990,145 A | 11/1999 | Wehner et al. | |
| 6,011,045 A | 1/2000 | Wehner et al. | |
| 6,043,265 A | 3/2000 | Murugesan et al. | |
| 6,414,002 B1 | 7/2002 | Cheng et al. | |
| 6,482,821 B2 | 11/2002 | Wehner et al. | |
| 2007/0093509 A1 | 4/2007 | Washburn et al. | |

FOREIGN PATENT DOCUMENTS

| | | |
|---|---|---|
| DE | 196 22 222 | 12/1997 |
| EP | 0 142 146 | 5/1985 |
| EP | 0 221 025 | 5/1987 |

(Continued)

OTHER PUBLICATIONS

Beccalli et al., Tetrahedron, 2005, 61(5), p. 1077-1082.*

(Continued)

Primary Examiner—Kamal A Saeed
Assistant Examiner—Yong Chu
(74) Attorney, Agent, or Firm—Maureen S. Gibbons; Burton Rodney

(57) ABSTRACT

The present application provides compounds, including all stereoisomers, solvates, prodrugs and pharmaceutically acceptable forms thereof according to Formula I

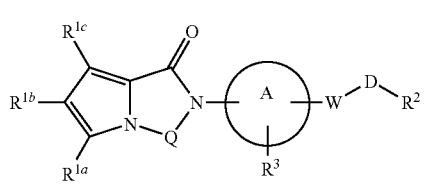

wherein $R^{1a}$, $R^{1b}$, $R^{1c}$, Q, A, $R^3$, W, D and $R^2$ are defined herein.

Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I.

28 Claims, No Drawings

FOREIGN PATENT DOCUMENTS

| | | |
|---|---|---|
| EP | 0 531 883 | 3/1993 |
| EP | 0 675 714 | 10/1995 |
| EP | 0 818 448 | 1/1998 |
| EP | 0 992 496 | 4/2000 |
| EP | 1 022 272 | 7/2000 |
| FR | 2 596 393 | 10/1987 |
| GB | 2 205 837 | 12/1988 |
| GB | 2 304 106 | 3/1997 |
| JP | 54-32794 | 10/1979 |
| JP | 04 297478 | 10/1992 |
| WO | WO 86/03488 | 6/1986 |
| WO | WO 94/15592 | 7/1994 |
| WO | WO 95/15954 | 6/1995 |
| WO | WO 97/21993 | 6/1997 |
| WO | WO 97/35576 | 10/1997 |
| WO | WO 97/48701 | 12/1997 |
| WO | WO 98/49899 | 11/1998 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/39077 | 7/2000 |
| WO | WO 00/50574 | 8/2000 |
| WO | WO 00/73288 | 12/2000 |
| WO | WO 02/10146 | 2/2002 |
| WO | WO 02/101146 | 12/2002 |
| WO | WO 03/033476 | 4/2003 |
| WO | WO 03/035624 | 5/2003 |
| WO | WO 2004/058762 | 7/2004 |
| WO | WO 2004/092181 | 10/2004 |
| WO | WO 2005/042541 | 5/2005 |
| WO | WO2005/085221 A | 9/2005 |
| WO | WO 2005/105805 | 11/2005 |

OTHER PUBLICATIONS

Vippagunta et al., Advanced Drug Delivery Reviews, p. 1.*
MCHR1, Wikipedia.*
STN search report-U.S. Appl. No. 11/671,150.*
Database WPI Week 200525, Derwent Publications Ltd., London, GB; AN 2005-242113: WO 2005/023782 A1 (Sankyo Co. Ltd.), Mar. 17, 2005, p. 95, compounds 9-138 (abstract).
Arnold, Z. et al., "Synthetic Reactions of Dimethylformamide. XXVII. A Simple Synthesis of Aminomalonaldehyde Derivatives", Collection Czechoslov. Chem. Commun., vol. 38, pp. 2633-2640 (1973).
Beccalli, E.M. et al., "Pd-catalyzed intramolecular cyclization of pyrrolo-2-carboxamides: regiodivergent routes to pyrrolo-pyrazines and pyrrolo-pyridines", Tetrahedron, vol. 61, pp. 1077-1082 (2005).
Bergman, J. et al., "Synthesis of Indoles via Ring Closure of 2-Alkylnitroaniline Derivatives", Tetrahedron, vol. 46, No. 17, pp. 6085-6112 (1990).
Berlin, A. et al., "3-Alkylthiopyrroles: Synthesis and Oxidative Polymerization to Conductive Materials", J. Chem. Soc. Perkin Trans. 2, pp. 699-704 (1990).
Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).
Biller, S.A. et al., "Squalene Synthase Inhibitors", Current Pharmaceutical Design, vol. 2, No. 1, pp. 1-40 (1996).
Boatman, R.J. et al., "Some Novel Reactions of Pyrrolecarboxylic Acid Chlorides", J. Org. Chem., vol. 41, No. 18, pp. 3050-3051 (1976).
Borowsky, B. et al., "Antidepressant, anxiolytic and anorectic effects of a melanin-concentrating hormone-1 receptor antagonist", Nature Medicine, vol. 8, No. 8, pp. 825-830 (2002).
Brimble, M.A. et al., "Synthesis of 2-Methylpyrrolo[1,2-$a$]pyrazin-1(2$H$)-one", Aust. J. Chem., vol. 41, pp. 1583-1590 (1988).

Budhram, R.S. et al., "$^{13}$C NMR Spectra of 2,3-Dihydro-1$H$-pyrrolo[1,2-$c$]imidazol-1,3-dione and its Thione Analogues", Organic Magnetic Resonance, vol. 13, No. 2, pp. 89-91 (1980).
Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).
Carpenter, A.J. et al., "Novel benzimidazole-based MCH R1 antagonists", Bioorganic & Medicinal Chemistry Letters, vol. 16, pp. 4994-5000 (2006).
Cory, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", Journal of the American Chemical Society, vol. 98, No. 5, pp. 1291-1293 (1976).
Focella, A. et al., "The Synthesis of Two Phenacetin Metabolites", Canadian Journal of Chemistry, vol. 50, pp. 2025-2030 (1972).
Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).
Gupton, J.T. et al., "Application of 2-Substituted Vinamidinium Salts to the Synthesis of 2,4-Disubstituted Pyrroles", J. Org. Chem., vol. 55, No. 15, pp. 4735-4740 (1990).
Handy, S.T. et al., "An unusual dehalogenation in the Suzuki coupling of 4-bromopyrrole-2-carboxylates", Tetrahedron Letters, vol. 44, pp. 427-430 (2003).
Hara, S., "Ileal Na$^+$/bile acid cotransporter inhibitors", Drugs of the Future, vol. 24, No. 4, pp. 425-430 (1999).
Hertzog, D.L. et al., "The discovery and optimization of pyrimidinone-containing MCH R1 antagonists", Bioorganic & Medicinal Chemistry Letters, vol. 16, pp. 4723-4727 (2006).
Iwanowicz, E.J. et al., "Inhibitors of Inosine Monophosphate Dehydrogenase: SARs about the $N$-[3-Methoxy-4-(5-oxazoly)phenyl Moiety", Bioorganic & Medicinal Chemistry Letters, vol. 13, pp. 2059-2063 (2003).
Jabin, I. et al., "Reaction of Cyclohexanone Benzylimines with Ethylidenemalonate Diesters. Diphenyl 2-Ethylidenemalonate: A Highly Eletrophilic Synthetic Equivalent of Crotonic Esters", J. Org. Chem., vol. 66, No. 1, pp. 256-261 (2001).
Katritzky, A.R. et al., "Novel Synthesis of Bicycles with Fused Pyrrole, Indole, Oxazole, and Imidazole Rings", J. Org. Chem., vol. 69, No. 26, pp. 9313-9315 (2004).
Kowalski, T.J. et al., "Melanin-concentrating hormone-1 receptor antagonism decreases feeding by reducing meal size", European Journal of Pharmacology, vol. 497, pp. 41-47 (2004).
Kowalski, T.J. et al., "Therapeutic potential of melanin-concentrating hormone-1 receptor antagonists for the treatment of obesity", Expert Opin. Investig. Drugs, vol. 13, No. 9, pp. 1113-1122 (2004).
Krause, B.R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).
Laxmi, Y.R.S. et al., "Chemoenzymatic Synthesis of Methyl (6$S$)-(−)-6,8-Dihydroxyoctanoate: A Precursor to ($R$)-(+)-α-Lipoic Acid", Synthesis, pp. 594-596 (1996).
Ljung, B. et al., "AZ 242, a novel PPARα/γ agonist with beneficial effects on insulin resistance and carbohydrate and lipid metabolism in ob/ob mice and obese Zucker rats", Journal of Lipid Research, vol. 43, pp. 1855-1863 (2002).
McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).
Negoro, T. et al., "Novel, Highly Potent Aldose Reductase Inhibitors: ($R$)-(−)-2-(4-Bromo-2-fluorobenzyl)-1,2,3,4-tetrahydropyrrolo[1,2-$a$]pyrazine-4-spiro-3'-pyrrolidine-1,2',3,5'-tetrone (AS-3201) and Its Congeners", J. Med. Chem., vol. 41, No. 21, pp. 4118-4129 (1998).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Papadopoulos, E.P., "Reactions of Phenyl Isothiocyanate with Metal Derivatives of Pyrrole", Journal of Organic Chemistry, vol. 31, pp. 3060-3062 (1966).

Papadopoulos, E.P., "Reactions of Pyrrole with Isocyanates. Preparation and Reactions of N-Ethoxycarbonylpyrrole-2-carboxamide and Pyrrole-1,2-dicarboximide", J. Org. Chem., vol. 37, No. 3, pp. 351-355 (1972).

Papadopoulos, E.P., "Reactions of Pyrrole with Isothiocyanates. Preparation and Reactions of N-Ethoxycarbonylpyrrole-2-thiocarboxamide and 2-Thiopyrrole-1,2-dicarboximide", J. Org. Chem., vol. 38, No. 4, pp. 667-674 (1973).

Papadopoulos, E.P. et al., "Reactions of Phenyl Isocyanate and Phenyl Isothiocyanate with Indole and Metal Derivatives of Indole", The Journal of Organic Chemistry, vol. 33, No. 12, pp. 4551-4554 (1968).

Papadopoulos, E.P. et al., "Reactions of Phenyl Isocyanate with Some Metal Derivatives of Pyrrole", Journal of Organic Chemistry, vol. 31, pp. 327-329 (1966).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of the Future, vol. 24, No. 1, pp. 9-15 (1999).

Sosa, A.C.B. et al., "Controlling cyclizations of 2-pyrrolecarboxamidoacetals. Facile salvation of β-amido aldehydes and revised structure of synthetic homolongamide", Tetrahedron Letters, vol. 41, pp. 4295-4299 (2000).

Souers, A.J. et al., "Identification of 2-(4-Benzyloxyphenyl)-N-[1-(2-pyrrolidin-1-yl-ethyl)-1H-indazol-6-yl]acetamide, an Orally Efficacious Melanin-Concentrating Hormone Receptor 1 Antagonist for the Treatment of Obesity", J. Med. Chem., vol. 48, No. 5, pp. 1318-1321 (2005).

Stout, D.M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity. Inhibitors of Acyl-CoA:Cholesterol Actyltransferase (ACAT). 7. Development of a Series of Substituted N-Phenyl-N'-[(1-phenylcyclopentyl)-methyl]ureas with Enhanced Hypocholestrolemic Activity", Chemtracts-Organic Chemistry, vol. 8, pp. 359-362 (1995).

Takekawa, S. et al., "T-226296: a novel, orally active and selective melanin-concentrating hormone receptor antagonist", European Journal of Pharmacology, vol. 438, pp. 129-135 (2002).

Ulven, T. et al., "6-Acylamino-2-aminoquinolines as Potent Melanin-Concentrating Hormone 1 Receptor Antagonists. Identification, Structure-Activity Relationship, and Investigation of Binding Mode", Journal of Medicinal Chemistry, vol. 48, No. 18, pp. 5684-5697 (2005).

Warshakoon, N.C. et al., "Design and synthesis of substituted quinolines as novel and selective melanin concentrating hormone antagonists as anti-obesity agents", Bioorganic & Medicinal Chemistry Letters, vol. 16, pp. 5207-5211 (2006).

Yajima, K. et al., "Combination therapy with PPARγ and PPARα agonists increases glucose-stimulated insulin secretion in db/db mice", Am. J. Physiol. Endocrinol. Metab., vol. 284, pp. E966-E971 and vol. 285, p. E926 (errata sheet) (2003).

Yang, Z. et al., "A facile route to N-fused pyrrole lactams", J. Indian Chem. Soc., vol. 80, pp. 790-791 (2003).

Carpenter, A. J. et al, "Melanin-concentrating hormone receptor antagonists as potential antiobesity agents", Expert Opinion on Therapeutic Patents, vol. 12, No. 11, pp. 1639-1646 (2002).

Chemical Abstracts, Database accession No. 1973:84249, "Pyrrole-1,2-dicarboxyimides".

* cited by examiner

MELANIN CONCENTRATING HORMONE RECEPTOR-1 ANTAGONISTS

This application claims priority from U.S. Provisional Application No. 60/765,530, filed Feb. 6, 2006, incorporated in its entirety herein by reference.

BACKGROUND OF THE INVENTION

Several lines of pharmacological and genetic evidence support the role of Melanin Concentrating Hormone Receptor-1 (hereafter "MCHR1") as a modulator of food intake and body weight. Central administration of MCH increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; Eur. J. Pharmacol., 438, 129-135, 2002, Nat. Med., 8, 825-830, 2002, Eur. J. Pharmacol., 497, 41-47, 2004.

DETAILED DESCRIPTION OF THE INVENTION

The present application provides compounds, including all stereoisomers, solvates, prodrugs and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression or anxiety by administration of a therapeutically effective dose of a compound according to Formula I.

Thus, in accordance with the present invention a compound is provided having the formula

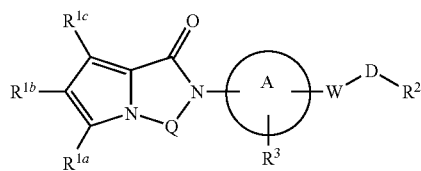

I wherein

A is selected from the group consisting of mono-cyclic aryl, mono-cyclic heteroaryl and bi-cyclic heteroaryl;

D is selected from the group consisting of a direct bond, alkyl, cycloalkyl and heterocyclyl;

Q is selected from the group consisting of $-(CR^8R^9)_n-$, $-C(R^8R^9)C(O)-$, $-C(O)C(R^8R^9)-$, $-(CO)_m-$, $-C(O)CR^8R^9C(O)-$, and $-CR^8=CR^9-$;

W is selected from the group consisting of a direct bond, $-C(O)-$, $-O-$, $-N(R^{9a})-$, $-S(O)-$, $-S(O_2)-$, $-S(O_2)N(R^{9a})-$ and $-C(R^{10})(R^{11})-$;

$R^{1a}$, $R^{1b}$ and $R^{1c}$ are independently selected from the group consisting of hydrogen, halo, aryl aryloxy, arylthio, arylalkylthio and heteroaryl, wherein the aryl and heteroaryl alone or as part of another group, may optionally and independently, be substituted with 1-3 $R^4$ groups;

$R^2$ is selected from the group consisting of hydrogen, hydroxyl, hydroxyalkyl, lower alkoxy, lower cycloalkoxy, $OCONR^7R^{7a}$, CN, $CONR^7R^{7a}$, $SOR^6$, $SO_2R^6$, $NR^7COR^{7b}$, $NR^7CO_2R^{7b}$, $CO_2R^6$, heterocyclyl, heteroaryl, $NR^7R^{7a}$, $NR^7SO_2R^6$ and $COR^6$;

$R^3$ is selected from the group consisting of hydrogen, hydroxyl, alkoxy, halo, CN, alkyl, perfluoroalkyl, cycloalkyl and cycloalkoxy, wherein $R^3$ and D may optionally be taken together with the atoms to which they are attached to form a 5 to 7-membered ring;

$R^4$ is selected from the group consisting of alkyl, halo, polyfluoroalkyl, alkoxy, polyfluoroalkyloxy, CN and alkylthio;

$R^6$ is independently selected from the group consisting of lower alkyl and lower cycloalkyl; and $R^7$, $R^{7a}$ and $R^{7b}$ are independently selected from the group consisting of hydrogen, lower alkyl and lower cycloalkyl, wherein two $R^7$ and the atom to which they are attached may optionally form a heterocyclyl of 4 to 7 atoms.

$R^8$, $R^9$, $R^{9a}$, $R^{10}$ and $R^{11}$ are independently selected from the group consisting of hydrogen and alkyl;

m is an integer from 1 to 2;

n is an integer from 1 to 4; or a pharmaceutically acceptable salt or a stereoisomer or a solvate or a prodrug ester thereof.

In one embodiment of the compounds of formula I of the invention Q is $-(CR^8R^9)_n-$ such as $CH_2CH_2$;

W is selected from the group consisting of a direct bond and $-O-$;

D is selected from the group consisting of a direct bond and alkyl such as $CH_2CH_2$, $CH_2CH_2CH_2$,

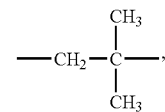

$CH_2$ or a bond;

$R^{1b}$ is aryl, such as phenyl, wherein the aryl is substituted with one $R^4$ substitutent at the para-position, or meta-position, and wherein the $R^4$ substitutent is selected from the group consisting of alkyl, halo and polyfluoroalkyl, such as p-Cl or p-$CF_3-$, and $R^{1a}$ and $R^{1c}$ are each H; or $R^{1b}$ is haloaryloxy such as p-Cl-phenoxy, or alkylphenyl, dihalophenyl, alkoxyphenyl or polyhaloalkoxy or alkylthiophenyl, such as 3,4-dichlorophenyl, p-methylphenyl, p-ethylphenyl, or p-n-propylphenyl, or p-methoxyphenyl, p-trifluoromethoxyphenyl, methylthiophenyl, or phenylalkylthio such as phenylalkylthio, or m-ethylphenyl; and $R^{1a}$ is H or halo such as Br; and $R^{1c}$ is H or halo such as Br;

A is aryl or heteroaryl, such as

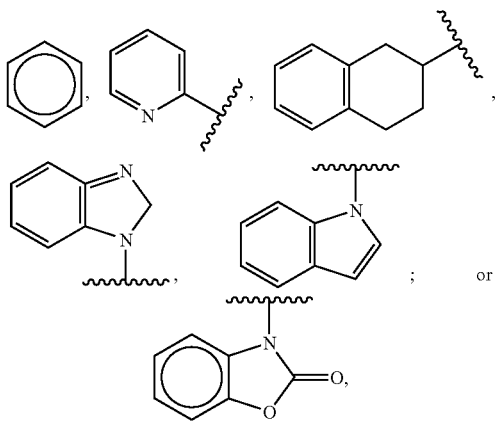

$R^3$ is selected from the group consisting of hydrogen, alkoxy, halo and alkyl, and where A is phenyl, $R^3$ is m-$CH_3O$, or p-$CH_3O$;

$R^2$ is heteroaryl, OH

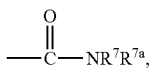

—$NR^7R^{7a}$ or heteroaryl, such as

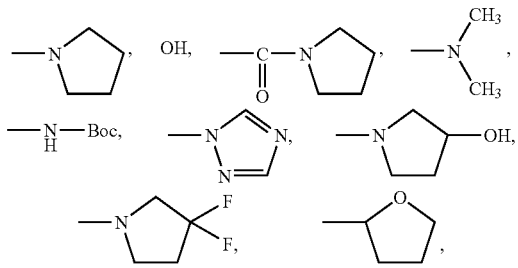

$NH_2$, or hydroxylalkyl such as

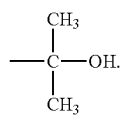

DEFINITIONS

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

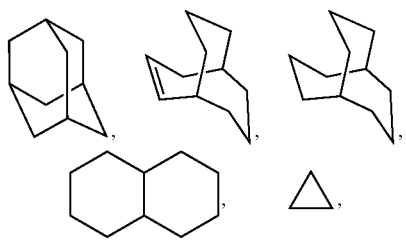

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

The term "heterocyclyl", as used herein, refers to an unsubstituted or substituted stable 4-, 5-, 6- or 7-membered monocyclic ring system which may be saturated or unsaturated, and which consists of carbon atoms and from one to four heteroatoms selected from N, O, S, SO and/or $SO_2$ group, wherein the nitrogen heteroatoms may optionally be oxidized, and the nitrogen heteroatom may optionally be quaternized. The heterocyclic ring may be attached at any heteroatom or carbon atom which results in the creation of a stable structure such as, for example, piperidinyl, piperazinyl, oxopiperazinyl, oxopiperidinyl and oxadiazolyl.

The term "alkanoyl" as used herein alone or as part of another group refers to alkyl linked to a carbonyl group.

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or "Aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings, for example

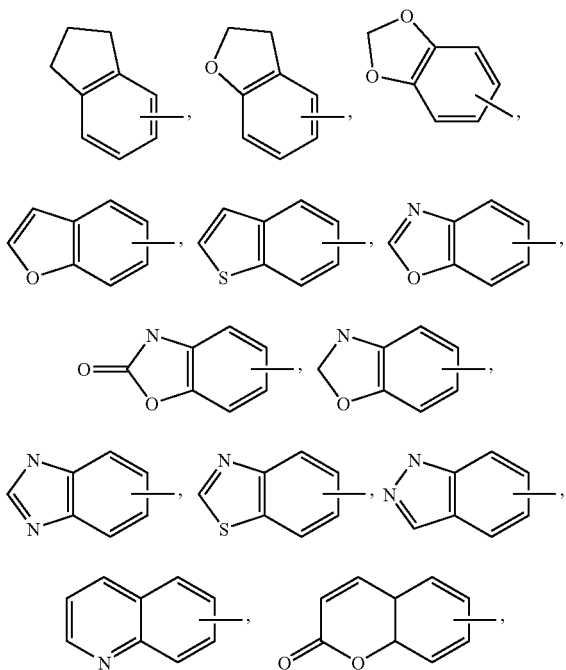

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

The term "heteroaryl" as used herein refers to a 5-, 6- or 7-membered aromatic heterocyclic ring which contains one or more heteroatoms selected from nitrogen, sulfur, oxygen and/or a SO or $SO_2$ group. Such rings may be fused to another ring such as, for example, cycloalkyl, cycloheteroalkyl, aryl or heteroaryl and include possible N-oxides.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

The term "polyhaloalkyl" as used herein refers to an "alkyl" group as defined above which includes from 2 to 9, preferably from 2 to 5, halo substituents, such as F or Cl, preferably F, such as polyfluoroalkyl, for example, $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, $CF_3CH_2O$, $CF_3O$ or $CF_3CF_2CH_2O$.

The compounds of Formula I of the application can be prepared as shown in the following reaction schemes and description thereof, as well as relevant published literature procedures that may be used by one skilled in the art. Exemplary reagents and procedures for these reactions appear hereinafter and in the working Examples.

ABBREVIATIONS

The following abbreviations are employed herein:
Ph=phenyl
Bn=benzyl
t-Bu=tertiary butyl
Me=methyl
Et=ethyl
TMS=trimethylsilyl
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3N$=triethylamine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Ar=argon
$N_2$=nitrogen
EDC=3-ethyl-3'-(dimethylamino)propyl-carbodiimide hydrochloride (or 1-[(3-(dimethyl)amino)propyl])-3-ethylcarbodiimide hydrochloride)
HOBT=1-hydroxybenzotriazole hydrate
DIC=1,3-dipropylcarbodiimide
PyBOP=benzotriazol-1-yloxy-tripyrrolidino phosphonium hexafluorophosphate
DDQ=2,3-Dichloro-5,6-dicyano-1,4-benzoquinone
min=minute(s)
h or hr=hour(s)
L=liter
mL=milliliter
µL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography LC/MS=high performance liquid chromatography/mass spectrometry
MS or Mass Spec=mass spectrometry
NMR=nuclear magnetic resonance
mp=melting point

METHODS OF PREPARATION

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

As summarized in Scheme 1, compounds of Formula I may be prepared by either of two general routes. The first approach entails either dialkylation, diacylation or alkylation/acylation of compounds of formula 1 with compounds of formula 2 (X=halogen, TsO, MsO, or OH) to generate the central bicyclic core. Equation 2 represents an alternative second approach entailing arylation of compounds of formula 3 containing a preformed central bicyclic core with arylating agents such as boronic acids of formula 4. Depending on the particular molecule of Formula I being prepared, $R^1$ s, $R^2$, $R^3$ and in particular the substituent W-D-$R^2$ can either be fully completed prior to or elaborated after assemblage of the core structure of Formula I.

SCHEME 1

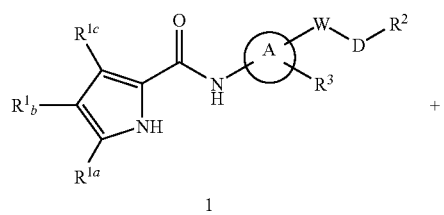

1

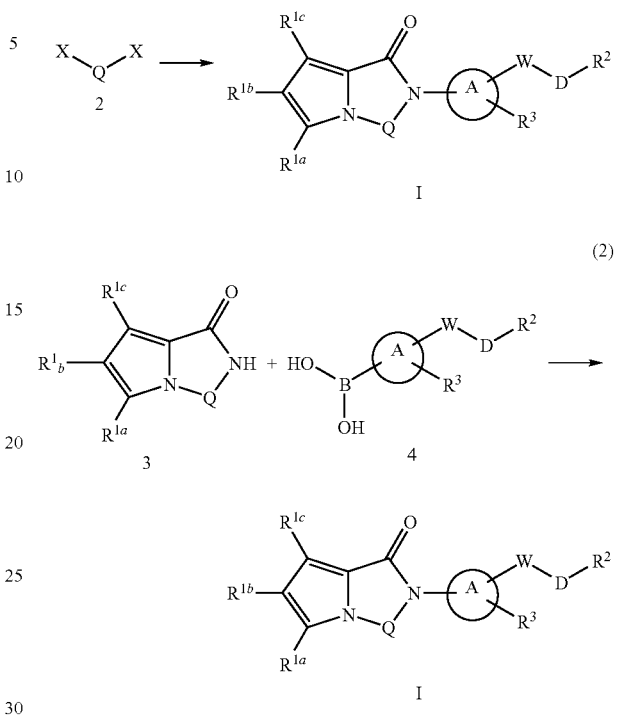

Syntheses of compounds of Formula I via equation 1 of Scheme 1 is specifically illustrated by the methods described in Scheme 2, 3 and 4. As shown in Scheme 2, the aryl or heteroaryl amines (formula 9) comprising the right-hand portion of compounds of Formula I may be synthesized by reduction of nitro aromatics of formula 8 either by catalytic hydrogenation using a catalyst such as Pd/C in a solvent such as EtOH or by reduction with $SnCl_2$ in a solvent such EtOAc. Compounds of formula 8 where W is O, S, N($R^9$), or C($R^{10}$) ($R^{11}$) can be prepared by alkylation of the corresponding phenols, thiophenols, anilines, phenylalkanes of formula 5 with an appropriate alkylating agent of formula 10 in the presence of a base such as $CS_2CO_3$, $K_2CO_3$, NaH, LDA etc. in a solvent such as DMF or THF by employing procedures readily known to those skilled in the art. Alternatively compounds of formula 8 where W is O, S, N($R^9$) can be prepared by heating compounds of formula 6 with preformed sodium salts of compounds of formula 11 in a solvent such as DMF. Compounds of formula 8 where W is $S(O_2)N(R^9)$, or C(O)$NR^9$ can be prepared by sulfonylation or acylation of amines of formula 12 with the corresponding sulfonyl chlorides and acyl chlorides of formula 7 in solvents such as $CH_2Cl_2$. Alternatively compounds of formula 8 where W is C(O)$NR^9$ can be prepared by acylation of amines of formula 12 with the corresponding acids of formula 7 in solvents such as $CH_2Cl_2$ in the presence of base such as triethylamine and coupling reagents such as EDC, DIC, PyBOP etc. Compounds of formula 8 where W is S(O), or $S(O_2)$ can be prepared by oxidation of thioethers of formula 8', which can be obtained from compounds of formula 5 or 6 employing the procedures described above, with oxidants such as MCPBA.

SCHEME 2

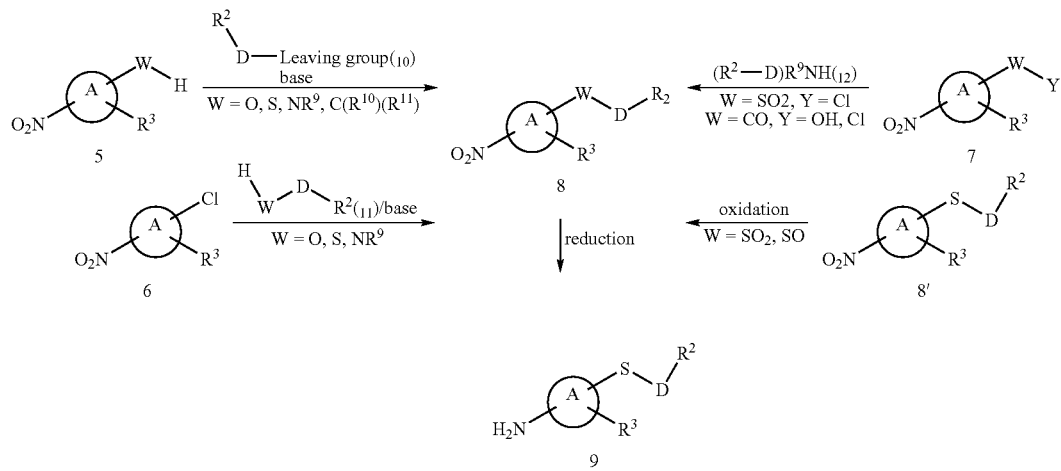

As shown in Scheme 3, the pyrrole carboxylic acids (formula 15) comprising the left-hand portion of compounds of Formula I may be synthesized by saponification of esters of formula 14 with a base such as NaOH, KOH etc. in solvent such as EtOH, MeOH etc., followed by acidification with HCl, $H_2SO_4$ etc. Esters of formula 14 can be synthesized from compounds of formula 13 which can be generated via Suzuki reaction or Stille reaction as described in *Tetrahedron Lett.* 2003, 44, 427 (Handy, et al.). When not commercially available, compounds of formula 13 can be made either from the corresponding methyl 1H-pyrrole-2-carboxylate by many synthetic transformations known to those skilled in the art or via cyclization of vinamidinium salts of formula 16 and methyl glycine ester using procedures of Gupton et al. *J. Org. Chem.* 1990, 55, 4735. Vinamidinium salts of formula 16 either are commercially available or can be synthesized by using the procedures of Davies et al. *J. Org. Chem.* 2001, 66, 251 (hexafluorophosphate salts) or the procedures of Arnold et al. *Collect. Czech. Chem. Commun.* 1973, 38, 2633 (perchlorate salts).

Scheme 4 describes both the amide bond formation between the aromatic amines of formula 9 with the pyrrole carboxylic acids of formula 15 to generate compounds of formula 1 using one of the variety procedures conducive to amide formation known to those skilled in the arts and the subsequent conversion of compounds of formula 1 to compounds of Formula I. Compounds of Formula I may be prepared by either dialkylation, alkylation/acylation, or diacylation of compounds of formula 1 with compounds of formula 2, which are commercially available or can be prepared using the procedures readily known to those skilled in the art. Suitable reaction conditions comprise stirring 1 and 2 in the presence of a base such as NaH, KOtBu, $Et_3N$, $iPr_2NEt$, $NaOH/Bu_4NBr$ etc., where X=halogen, OTs, OMs, alkoxy (for esters), by using coupling condition, such as EDC, PyBop, etc. where X=OH and compound of formula 2 is at least a mono-carboxylic acid, or by employing Mitsunobu condition where X=OH and compound of formula 2 is at least mono-alcohol. Alternatively compounds of Formula I where Q=—C(O)— may be synthesized by heating of compounds

SCHEME 3

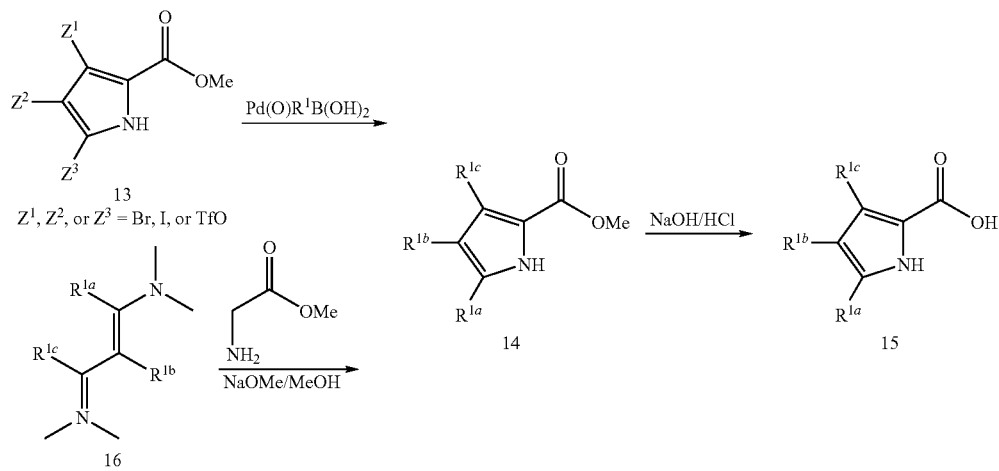

of formula 1 with phenylisocyante in the presence of TEA (Papadopoulos et al. *J. Org. Chem.* 1968, 33, 4551).

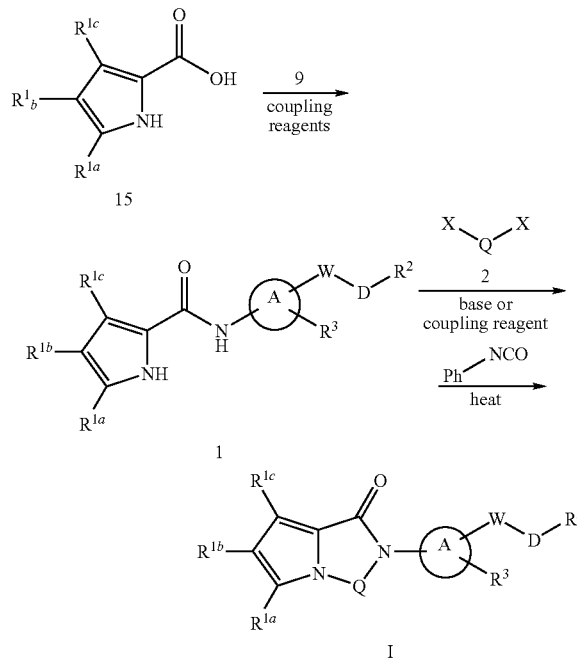

SCHEME 4

Scheme 5 outlines the synthesis of compounds of Formula I by the alternative approach 2 of Scheme 1. Compounds of Formula I may be prepared by arylation of compounds of formula 3 with an aryl boronic acid of formula 4 in the presence of $Cu(OAc)_2$ in a solvent such as $CH_2Cl_2$ containing molecular sieves. Compounds of formula 3 can be prepared by following the procedure described in Scheme 4 via amide formation of acids of formula 15 with ammonia and the subsequent dialkylation, alkylation/acylation, or diacylation. Alternatively compounds of formula 3, where Q is —$(CR^8R^9)_n$—, can be prepared by alkylation reaction of esters of formula 14 with dibromides of formula 2 (X=Br) to form mono-bromo esters and the subsequent tandem alkylation/acylation reaction of the corresponding mono-bromo eaters with ammonia in the presence of a base such as NaOH/$Bu_4NBr$ (Yang, Z., et al. *J. Indian Chem. Soc.* 2003, 80, 790). Aryl boronic acids of formula 4 are commercially available or can be formed by treating commercially available compounds of formula 17 either with n-BuLi in a solvent such as THF followed by sequential addition $B(OMe)_3$ and then hydrolysis with hydrochloric acid or alternatively stirring 17 with diborate 18 in the presence of a Pd catalyst followed by transesterification with benzaldehyde in the presence of hydrochloric acid. It should be noted the synthesis of compounds of Formula I via this approach can be greatly facilitated if the substituent W-D-$R^2$ of compound of formula 17 is replaced with W capped with a protecting group which, after transformation of 17 to compounds of Formula I, is sequentially deprotected and alkylated to generate the fully elaborated appendage W-D-$R^2$ using methods known to those skilled in the arts.

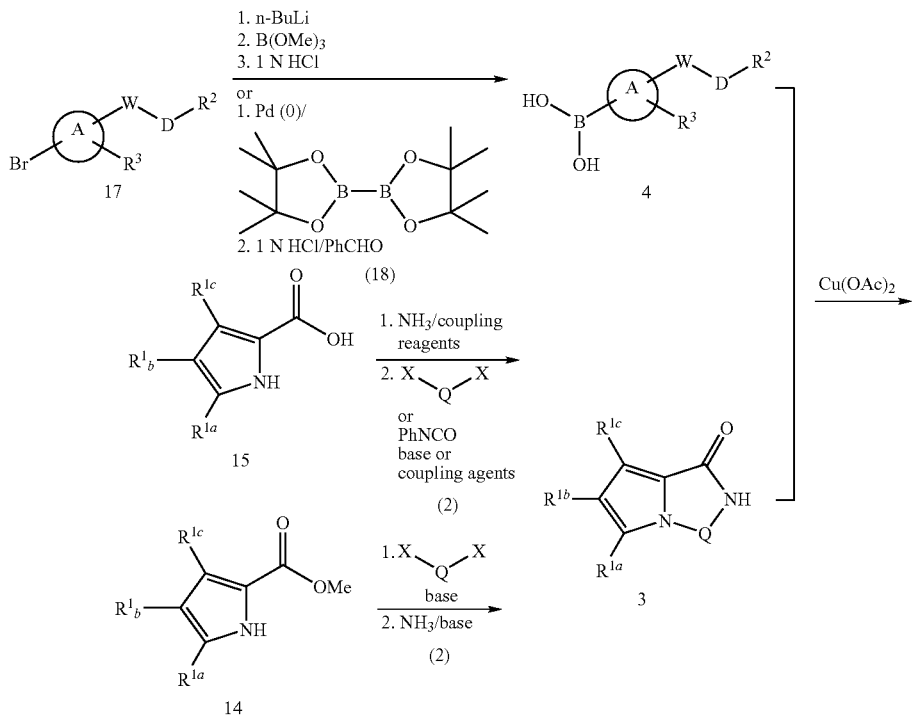

SCHEME 5

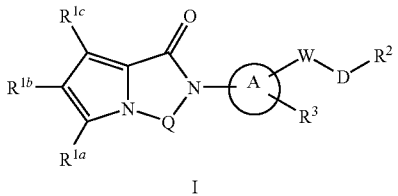

I

As illustrated in Scheme 6, compounds of Formula I', where Q is —C($R^3$)═C($R^9$)—, may be prepared by either of two synthetic approaches. The first one involves oxidation of compounds of Formula I where Q is —CHR$^8$—CHR$^9$— with oxidants such as $MnO_2$ (see, Brimble et al. Aus. J. Chem. 1988, 41, 1583), DDQ etc. An alternative approach to generate compounds of Formula I' utilizes an intramolecular condensation of compounds of formula 22 in the presence of an acid such as $CH_3SO_3H$ (Sosa, et al. *Tetrahedron Lett.* 2000, 41, 4295), $H_2SO_4$ etc. Compounds of formula 22 can be synthesized by deprotection of cyclic or acyclic acetal/ketal of formula 21 with the appropriate reagents such as TsOH/ actone/$H_2O$ etc. well familiar to those skilled in the art (other typical examples may be found in Greene, T and Wuts, P. G. M., *Protecting Groups in Organic Synthesis*, John Wiley & Sons, Inc., New York, N.Y., 1999 and references therein). Compounds of formula 21 can be prepared by coupling of secondary aromatic amines of formula 20 with acids of formula 15 in solvents such as $CH_2Cl_2$ in the presence of base such as triethylamine and coupling reagents such as EDC, DIC, PyBOP etc. Aromatic amines of formula 20 can be prepared via alkylation of primary aromatic amines 9 with compounds of formula 19, which are commercially available or can be made by many synthetic methodologies readily recognizable by those skilled in the art.

SCHEME 6

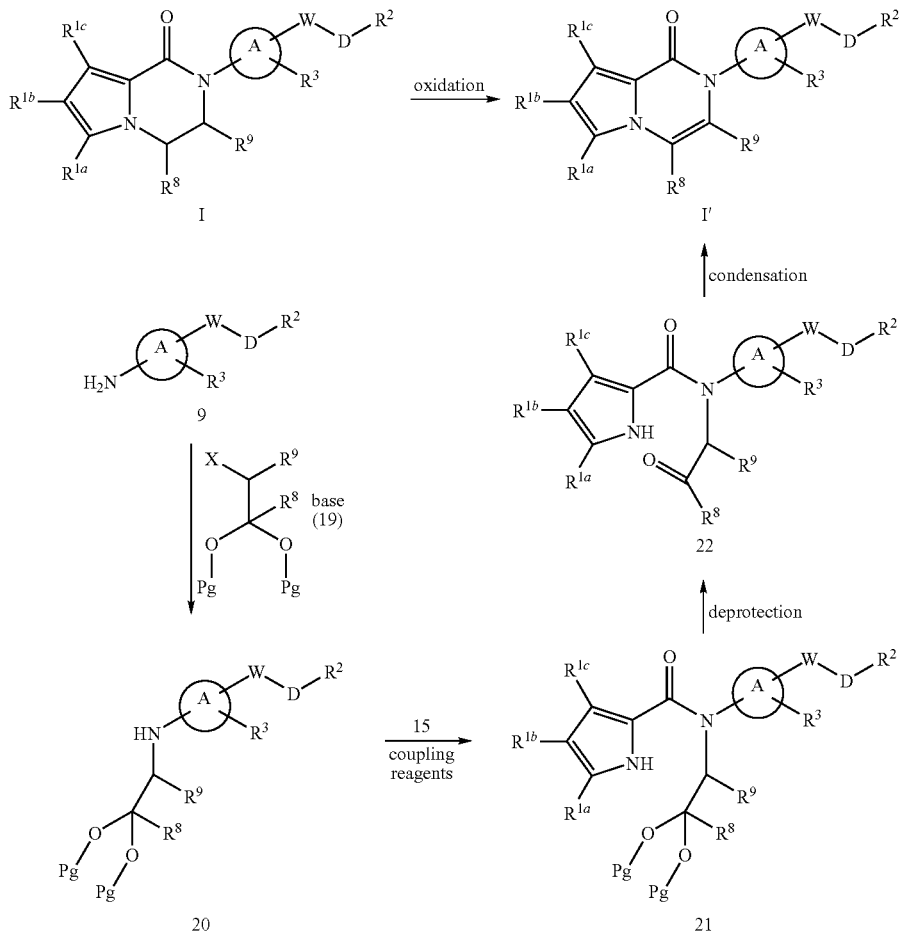

The term "prodrug" encompasses both the term "prodrug esters" and the term "prodrug ethers". The term "prodrug esters" as employed herein includes esters and carbonates formed by reacting one or more hydroxyls of compounds of Formula I with either alkyl, alkoxy, or aryl substituted acylating agents or phosphorylating agent employing procedures known to those skilled in the art to generate acetates, pivalates, methylcarbonates, benzoates, amino acid esters, phosphates and the like.

Examples of such prodrug esters include

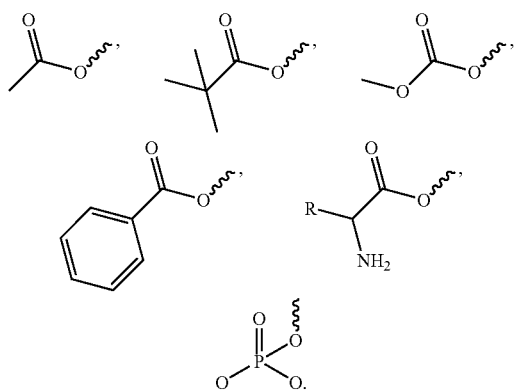

The term "prodrug ethers" include both phosphate acetals and O-glucosides. Representative examples of such prodrug ethers include

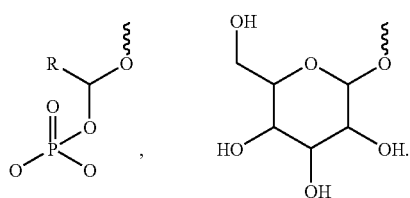

The compounds of Formula I can be present as salts, which are also within the scope of this invention. Pharmaceutically acceptable (i.e., non-toxic, physiologically acceptable) salts are preferred. If the compounds of Formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

All stereoisomers of the compound of the instant application are contemplated, either in admixture or in pure or substantially pure form. The compound of the present application can have asymmetric centers at any of the carbon atoms including any one of the R substituents. Consequently, compound of Formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

EXAMPLES

The following Examples serve to better illustrate, but not limit, some of the preferred embodiments of the application.

Example 1

Preparation of 7-(4-chlorophenyl)-2-(3-methoxy-4-(2-(pyrrolidin-1-yl)ethoxy)phenyl)-3,4-dihydropyrrolo[1,2-a]pyrazin-1(2H)-one trifluoroacetic acid salt

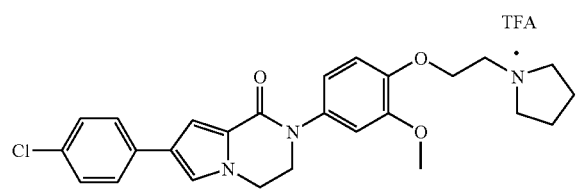

Step A. Preparation of methyl 4-(4-chlorophenyl)-1H-pyrrole-2-carboxylate

To a stirred DMF solution (40 mL) containing methyl 4-bromo-1H-pyrrole-2-carboxylate (1.0 g, 4.9 mmol), commercially available from Bionet, and Pd(Ph$_3$)$_4$ (195 mg, 0.17 mmol) was added Na$_2$CO$_3$ (1.3 g, 12.52 mmol) (dissolved in minimum amount water) and 4-chlorophenyl boronic acid (0.85 g, 5.43 mmol) under Ar. The mixture was degassed with Ar prior to stirring overnight at 110° C. After cooling the reaction to RT, it was diluted with 10 mL of water and 200 mL of EtOAc. The aqueous layer was extracted with EtOAc (3×20 mL). The organic layers were combined, dried over Na$_2$SO$_4$, and conc. in vacuo to yield a brown oil. The oil was purified by column chromatography (silica gel, 0%-15% gradient elution with EtOAc/hexanes) to yield 288 mg (25%) of product as white solid. MS (ESI) 236 (M+H)+.

Step B. Preparation of 4-(4-chlorophenyl)-1H-pyrrole-2-carboxylic acid

A 95:5 EtOH/H$_2$O solution (5.0 mL) containing methyl 4-(4-chlorophenyl)-1H-pyrrole-2-carboxylate (120 mg, 0.51 mmol) and NaOH (1.53 mol) was refluxed for 2 h whereupon the EtOH was removed in vacuum. After removal of traces of EtOH by azotroping twice with water, acidification to pH 3 with 1 M HCl generated a white precipitate. The precipitate was collected by filtration, washed with water, and dried in vacuum to give 110 mg (98%) of the title compound as a white solid. MS (ESI) 222 (M+H)+.

Step C. Preparation of 4-(4-chlorophenyl)-N-(3-methoxy-4-(2-(pyrrolidin-1-yl)ethoxy)phenyl)-1H-pyrrole-2-carboxamide Following preparation as described in Patent: WO2002/101146, 3-methoxy-4-(2-(pyrrolidin-1-yl)ethoxy)benzenamine (59 mg, 0.25 mol) was stirred overnight in DMF (2 mL) containing with 4-(4-chlorophenyl)-1H-pyrrole-2-carboxylic acid (65 mg, 0.25 mol), EDC (96 mg, 0.50 mol), HOBT (77 mg, 0.50 mol) and NaHCO$_3$ (116 mg, 1.37 mol). After dilution of the reaction with 40 mL of EtOAc, the organic layer was washed with H$_2$O (10 mL×2) and brine. The organic layer was dried over Na$_2$SO$_4$, and conc. in vacuum to a brown oil. The oil was purified by flash column chromatography (silica gel, CH$_3$OH in CH$_2$Cl$_2$, 0-10% gradient) to yield 109 mg (99%) of the title compound as a colorless oil. MS (ESI) 440 (M+H)+.

Step D. Preparation of 7-(4-chlorophenyl)-2-(3-methoxy-4-(2-(pyrrolidin-1-yl)ethoxy)phenyl)-3,4-dihydropyrrolo[1,2-a]pyrazin-1(2H)-one trifluoroacetic acid salt A mixture of 4-(4-chlorophenyl)-N-(3-methoxy-4-(2-(pyrrolidin-1-yl)ethoxy)phenyl)-1H-pyrrole-2-carboxamide (30 mg, 0.068 mol), 1,2-dibromoethane (0.15 mL, 1.70 mol), 1 N NaOH (0.2 mL, 0.2 mL) and tetrabutyl ammonium bromide (22 mg 0.068 mol) was stirred overnight. The reaction was diluted with 10 mL of EtOAc, washed with sat. NH$_4$Cl solution (2×3 mL). The organic layer was dried over Na$_2$SO$_4$ prior to concentration in vacuum to a brown oil. The oil was purified by prep reverse phase HPLC (Phenomenex Luna 5u C18 21.2×100, H$_2$O/MeOH/0.1% TFA) to yield 37 mg (94%) of the product as a tan lyophilate. MS (ESI) 466 (M+H)+.

Step D'. Alternative preparation of 7-(4-chlorophenyl)-2-(3-methoxy-4-(2-(pyrrolidin-1-yl)ethoxy)phenyl)-3,4-dihydropyrrolo[1,2-a]pyrazin-1(2H)-one trifluoroacetic acid salt To a solution of 4-(4-chlorophenyl)-N-(3-methoxy-4-(2-(pyrrolidin-1-yl)ethoxy)phenyl)-1H-pyrrole-2-carboxamide (30 mg, 0.068 mol) in 1 mL of DMF was sequentially added NaH (60% in mineral oil, 3.27 mg, 0.082 mol) and 1,2-dibromoethane (5.86 uL, 0.068 mol). While the stirred reaction was maintained at 80° C. for 60 min, NaH (60% in mineral oil, 3.27 mg, 0.082 mol) and 1,2-dibromoethane (5.86 uL, 0.068 mol) were added to the reaction mixture every 20 min. The reaction was cooled to 0° C., quenched with H$_2$O, and concentrated to a brown oil. The oil was taken up with MeOH and purified by prep HPLC (Phenomenex Luna 5u C18 21.2×100, H$_2$O/MeOH/0.1% TFA) to yield 5.4 mg (14%) of the title compound as a tan lyophilate. MS (ESI) 466 (M+H)+.

Example 2

Preparation of 7-(4-trifluoromethylphenyl)-2-(3-methoxy-4-(2-(pyrrolidin-1-yl)ethoxy)phenyl)-3,4-dihydropyrrolo[1,2-a]pyrazin-1(2H)-one trifluoroacetic acid salt

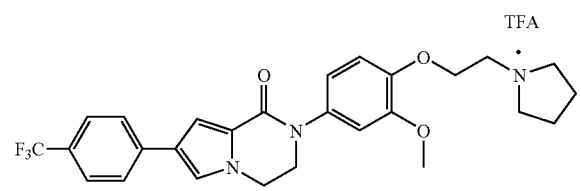

Step A. Preparation of 4-bromo-1H-pyrrole-2-carboxylic acid

Methyl 4-bromo-1H-pyrrole-2-carboxylate was converted to the title compound in 99% yield following the procedure described in step B of Example 1. MS (ESI) 190, 192 (M+H)+.

Step B. Preparation of 4-bromo-N-(3-methoxy-4-(2-(pyrrolidin-1-yl)ethoxy)phenyl)-1H-pyrrole-2-carboxamide 4-Bromo-1H-pyrrole-2-carboxylic acid was converted to the title compound in 91% yield following the procedure described in step B of Example 1. MS (ESI) 408, 410 (M+H)+.

Step C. Preparation of 7-bromo-2-(3-methoxy-4-(2-(pyrrolidin-1-yl)ethoxy)phenyl)-3,4-dihydropyrrolo[1,2-a]pyrazin-1(2H)-one The title compound was prepared by alkylating the carboxamide of step B with 1,2-dibromoethane via the procedure described in step D of Example 1 in 95% yield. MS (ESI) 434, 436 (M+H)+.

Step D. Preparation of 7-(4-trifluoromethylphenyl)-2-(3-methoxy-4-(2-(pyrrolidin-1-yl)ethoxy)phenyl)-3,4-dihydropyrrolo[1,2-a]pyrazin-1(2H)-one trifluoroacetic acid salt Following the procedure described in step A of Example 1, a Suzuki coupling between 4-bromo-N-(3-methoxy-4-(2-(pyrrolidin-1-yl)ethoxy)phenyl)-1H-pyrrole-2-carboxamide (20 mg) and 4-trifluoromethylphenyl boronic acid (13 mg) yielded the title compound (1.3 mg). MS (ESI) 500 (M+H)+.

Example 3

Preparation of 8-(4-chlorophenyl)-2-(3-methoxy-4-(2-(pyrrolidin-1-yl)ethoxy)phenyl)-2,3,4,5-tetrahydropyrrolo[1,2-a][1,4]diazepin-1-one trifluoroacetic acid salt

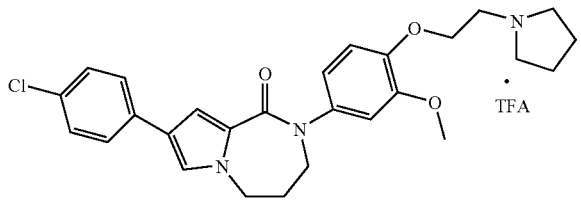

Following the procedure described in step D' of Example 1, 4-(4-chlorophenyl)-N-(3-methoxy-4-(2-(pyrrolidin-1-yl)ethoxy)phenyl)-1H-pyrrole-2-carboxamide (30 mg, 0.068 mol), preparation described in step C of Example 1, was alkylated with 1,3-dibromopropane (5.86 uL, 0.068 mol) to yield the title compound in 9% yield. MS (ESI) 480 (M+H)$^+$.

Example 4

Preparation of 7-(4-chlorophenyl)-2-(4-(2-hydroxy-2-methylpropoxy)-3-methoxyphenyl)-3,4-dihydropyrrolo[1,2-a]pyrazin-1(2H)-one

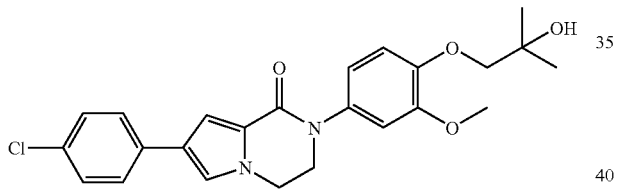

Step A. Preparation of 1-(2-methoxy-4-aminophenoxy)-2-methylpropan-2-ol

A sealed 25 mL vial containing the potassium salt of 2-methoxy-4-nitrophenol (1.15 g, 5.5 mol), NaH$_2$PO$_4$ (650 mg, 5.4 mol) and isobutylene oxide (550 mg, 7.8 mol) in 15% H$_2$O/MeCN (15 mL) was heated in a microwave at 170° for 80 min while being stirred. By HPLC the API for the product 1-(2-methoxy-4-nitrophenoxy)-2-methylpropan-2-ol was 96% whereas that of the starting phenol was 4%. After removal of the volatiles under vacuum, the residue was portioned between CH$_2$Cl$_2$ and aq. Na$_2$CO$_3$. Following separation of the layers, the aq phase was extracted 2× with CH$_2$Cl$_2$. The combined CH$_2$Cl$_2$ layers were washed 3× with aq Na$_2$CO$_3$ and 1× with brine prior to drying over Na$_2$SO$_4$. After removal of the volatiles under vacuum, 1.2 g (90%) of tertiary alcohol was isolated as a light tan solid. The above product, upon dissolution in EtOH (30 mL) and addition of 50 mg of 10% Pd/C, was hydrogenated at 53 psi of H$_2$ for 3 hr. Upon HPLC confirmation of completion, the reaction was filtered through celite which was subsequently washed with more EtOH. The combined EtOH filtrate was concentrated under vacuum to yield 1.1 g of the title compound which was carried forward without further purification.

Step B. Preparation of 4-(4-chlorophenyl)-N-(4-(2-hydroxy-2-methylpropoxy)-3-methoxyphenyl)-1H-pyrrole-2-carboxamide 1-(2-methoxy-4-aminophenoxy)-2-methylpropan-2-ol was converted to the title compound (18 mg) by acylation with 4-(4-chlorophenyl)-1H-pyrrole-2-carboxylic (21 mg) acid following the procedure described in step C of Example 1. MS (ESI) 415 (M+H)$^+$.

Step C. Preparation of 7-(4-chlorophenyl)-2-(4-(2-hydroxy-2-methylpropoxy)-3-methoxyphenyl)-3,4-dihydropyrrolo[1,2-a]pyrazin-1(2H)-one Following the procedure described in Example 1 step D, the product of step B (11 mg) was alkylated with 1,2-dibromoethane to yield 1.8 mg of the title compound. MS (ESI) 441 (M+H)$^+$.

Example 5

Preparation of 7-(4-chlorophenyl)-2-(6-(2-(pyrrolidin-1-yl)ethoxy)pyridin-3-yl)-3,4-dihydropyrrolo[1,2-a]pyrazin-1(2H)-one di-trifluoroacetic acid salt

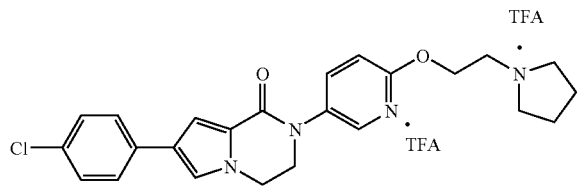

Step A. Preparation of 5-amino-2-((pyrrolidin-1-yl)ethoxy)pyridine

To a stirred DMF solution (25 mL) containing N-(2-hydroxyethyl)pyrrolidine (2.18 g, 18.9 mmol) under N$_2$ was added 60% NaH in mineral oil (0.76 g, 18.9 mmol). The mixture was stirred for 1 hr while gas evolution ceased. Subsequently 2-chloro-5-nitropyridine (2.0 g, 12.6 mmol) was added. After stirring overnight, the dark solution was poured into H$_2$O (100 mL) and extracted 3× with EtOAc. The combined organic layers were washed 2× with H$_2$O prior to drying over Na$_2$SO$_4$. Concentration under vacuum yielded an orange oil which was chromatographed on silica gel employing ~10% MeOH/CH$_2$Cl$_2$ to elute 1.62 g of 5-nitro-2-(pyrrolidin-1-yl)-ethoxy)pyridine (54%). The above product reduced to the corresponding substituted aminopyridine by hydrogenation in an EtOH solution (20 mL) containing 10% Pd/C (0.1 g) under 60 psi of H$_2$ for 4 hr. Upon completion the reaction was filtered prior to concentration under vacuum. The resulting dark oil was chromatographed on silica. Gradient elution (CH$_2$CL$_2$ to 20% MeOH/CH$_2$Cl$_2$) eluted 1.03 g of the title compound as a broad peak.

Step B. Preparation of 4-(4-chlorophenyl)-N-(6-(2-(pyrrolidin-1-yl)ethoxy)pyridin-3-yl)-1H-pyrrole-2-carboxamide 5-Amino-2-((pyrrolidin-1-yl)ethoxy)pyridine was converted to the title compound (18 mg) by acylation with 4-(4-chlorophenyl)-1H-pyrrole-2-carboxylic acid (21 mg) following the procedure described in step C of Example 1. MS (ESI) 411 (M+H)$^+$.

Step C. Preparation of 7-(4-chlorophenyl)-2-(6-(2-(pyrrolidin-1-yl)ethoxy)pyridin-3-yl)-3,4-dihydropyrrolo[1,2-a]pyrazin-1(2H)-one di-trifluoroacetic acid salt Following the procedure described in Example 1 step D, 4-(4-chlorophenyl)-N-(6-(2-(pyrrolidin-1-yl)ethoxy)pyridin-3-yl)-1H-pyrrole-2-carboxamide (10.3 mg) was alkylated with 1,2-dibromoethane to yield 5.5 mg of the title compound. MS (ESI) 437 (M+H)$^+$.

Example 6

Preparation of 7-(4-chlorophenyl)-2-(3-methoxy-4-(2-oxo-2-(pyrrolidin-1-yl)ethoxy)phenyl)-3,4-dihydropyrrolo[1,2-a]pyrazin-1(2H)-one

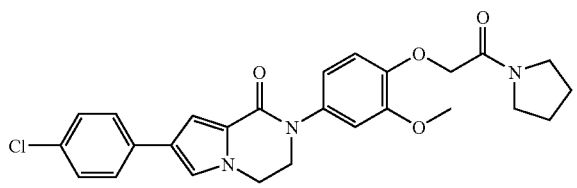

Step A. Preparation of 2-hydroxy-1-(pyrrolidin-1-yl)ethanone

Pyrrolidine (3.0 mL; 35.9 mmol) was added to glycolic acid (2.73 g; 35.9 mmol) over 5 minutes while cooling in an ice bath. The suspension was diluted with o-xylene (3.5 mL) and heated to reflux for 7 h whereupon the o-xylene was removed by distillation to afford the title compound (4.17 g; 90%) as an orange oil. $^1$H NMR (CDCl$_3$) δ 1.86-1.92 (m, 2H), 1.96-2.02 (m, 2H), 3.26-3.29 (m, 2H), 3.52-3.55 (m, 3H), 4.08 (s, 2H); $^{13}$C NMR (CDCl$_3$) δ 23.94, 25.74, 44.26, 45.96, 60.48, 169.90.

Step B. Preparation of 2-(2-methoxy-4-nitrophenoxy)-1-(pyrrolidin-1-yl)ethanone To a stirred solution of DMF (20 mL) containing 2-hydroxy-1-(pyrrolidin-1-yl)ethanone (2.00 g, 15.5 mmol) under N$_2$ was added 60% NaH/paraffin (640 mg, 16 mmol). Once gas evolution ceased, 2-chloro-5-nitroanisole (1.9 g, 10 mmol) was added. After stirring for 18 hr at 20°, the reaction was diluted with H$_2$O prior to being extracted with EtOAc 3×. The organic layers were washed twice with aq. Na$_2$CO$_3$, brine and dried over Na$_2$SO$_4$ prior to concentration. Chromatography on silica gel using 25% EtOAc/CH$_2$Cl$_2$ eluted 2.06 g of 2-(2-methoxy-4-nitrophenoxy)-1-(pyrrolidin-1-yl)ethanone (52%). $^1$H NMR (DMSO-d$_6$) δ 1.73-1.79 (m, 2H), 1.86-1.92 (m, 2H), 3.29-3.32 (m, 2H), 3.43-3.46 (m, 2H), 3.04 (s, 3H), 4.93 (s, 2H), 7.02 (d, J=8.80 Hz, 1H), 7.73 (d, J=2.74 Hz, 1H), 7.84 (dd, J=8.80 Hz, 2.20 Hz, 1H); $^{13}$C NMR (DMSO-d$_6$) δ 23.22, 25.35, 44.27, 45.30, 55.76, 66.23, 106.35, 111.93, 116.99, 140.51, 148.25, 153.28, 164.33; HPLC a) column: Phenomenex C18 4.6×50 mm, 4 min gradient, 10% MeOH/90% H$_2$O/0.2% H$_3$PO$_4$ to 90% MeOH/10% H$_2$O/0.2% H$_3$PO$_4$; 1 min hold, 4 mL/min UV detection at 220 nm, 2.24 min retention time, (100%); HPLC b) column: Phenomenex C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 2.29 min retention time; MS (ES): m/z 281 (M+H)$^+$.

Step C. Preparation of 2-(4-amino-2-methoxyphenoxy)-1-(pyrrolidin-1-yl)ethanone A suspension of 2-(2-methoxy-4-nitrophenoxy)-1-(pyrrolidin-1-yl)ethanone (2.03 g; 7.24 mmol) and 10% Pd(C) (1.54 g; 1.45 mmol) in EtOH (20 mL) was hydrogenated at 55 psi of H$_2$ for 5 h. After filtration through fiberglass filter paper, the filtrate was concentrated under reduced pressure. The residue was purified by flash chromatography (silica gel, CH$_2$Cl$_2$/CH$_3$OH, 100:0 to 19:1 gradient) to afford the title compound (1.54 g; 85%) as an orange gum. $^1$H NMR (CDCl$_3$) δ 1.81-1.86 (m, 2H), 1.91-1.96 (m, 2H), 3.49-3.56 (m, 6H), 3.81 (s, 3H), 4.58 (s, 2H), 6.19 (dd, J=8.80 Hz, 2.20 Hz, 1H), 6.30 (d, J=2.75 Hz, 1H), 6.81 (d, J=8.80 Hz, 1H); $^{13}$C NMR (CDCl$_3$) δ 23.78, 26.22, 45.90, 46.10, 55.73, 70.47, 100.70, 106.54, 117.06, 140.41, 142.01, 150.69, 167.13; HPLC a) column: Phenomenex C18 4.6×50 mm, 4 min gradient, 10% MeOH/90% H$_2$O/0.2% H$_3$PO$_4$ to 90% MeOH/10% H$_2$O/0.2% H$_3$PO$_4$; 1 min hold, 4 mL/min UV detection at 220 nm, 0.19, 0.66 min retention time, (98%); HPLC b) column: Phenomenex C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 0.99 min retention time; MS (ES): m/z 251 (M+H)$^+$.

Step D. Preparation of 4-(4-chlorophenyl)-N-(3-methoxy-4-(2-oxo-2-(pyrrolidin-1-yl)ethoxy)phenyl)-1H-pyrrole-2-carboxamide Acylation of 2-(4-amino-2-methoxyphenoxy)-1-(pyrrolidin-1-yl)ethanone with 4-(4-chlorophenyl)-1H-pyrrole-2-carboxylic acid to generate the title compound was achieved following the procedure described in step C of Example 1 in 95% yield. MS (ESI) 401 (M+H)$^+$.

Step E. Preparation of 7-(4-chlorophenyl)-2-(3-methoxy-4-(2-oxo-2-(pyrrolidin-1-yl)ethoxy)phenyl)-3,4-dihydropyrrolo[1,2-a]pyrazin-1(2H)-one Following the procedure described in Example 1 step D, 4-(4-chlorophenyl)-N-(3-methoxy-4-(2-oxo-2-(pyrrolidin-1-yl)ethoxy)phenyl)-1H-pyrrole-2-carboxamide (11 mg) was alkylated with 1,2-dibromoethane to yield 9.2 mg of the title compound. MS (ESI) 480 (M+H)$^+$.

Example 7

Preparation of 7-(4-chlorophenyl)-2-(6-((dimethylamino)methyl)-5,6,7,8-tetrahydronaphthalen-2-yl)-3,4-dihydropyrrolo[1,2-a]pyrazin-1(2H)-one bis-trifluoroacetic acid salt

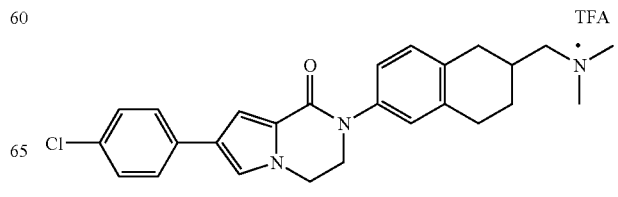

Step A. Preparation of 4-(4-chlorophenyl)-N-(6-((dimethylamino)methyl)-5,6,7,8-tetrahydronaphthalen-2-yl)-1H-pyrrole-2-carboxamide Following preparation as described in WO03087046, 6-((dimethylamino)methyl)-5,6,7,8-tetrahydronaphthalen-2-amine was converted to the title compound (8 mg) by acylation with 4-(4-chlorophenyl)-1H-pyrrole-2-carboxylic acid (25 mg) following the procedure described in step C of Example 1. MS (ESI) 408 (M+H)$^+$.

Step B. Preparation of 7-(4-chlorophenyl)-2-(6-((dimethylamino)methyl)-5,6,7,8-tetrahydronaphthalen-2-yl)-3,4-dihydropyrrolo[1,2-a]pyrazin-1(2H)-one di-trifluoroacetic acid salt Following the procedure described in Example 1 step D, the above product of step A (8.0 mg) was alkylated with 1,2-dibromoethane to yield 2.5 mg of the title compound. MS (ESI) 434 (M+H)$^+$.

Example 8

Preparation of 7-(4-chlorophenyl)-2-(4-(2-(pyrrolidin-1-yl)ethoxy)phenyl)-3,4-dihydropyrrolo[1,2-a]pyrazin-1(2H)-one trifluoroacetic acid salt

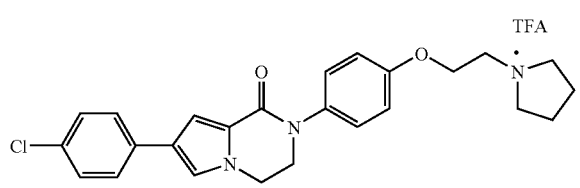

Step A. Preparation of 4-(2-(pyrrolidin-1-yl)ethoxy)benzenamine

A stirred DMF suspension (5 mL) of 4-nitrophenol (0.5 g, 3.6 mmol), 1-(2-chloroethyl)pyrrolidine hydrochloride (0.92 (5.4 mmol) and K$_2$CO$_3$ (1.24 g, 9 mmol) was heated at 80 for 3 hr. After cooling to RT, the reaction was diluted with H$_2$O and extracted 3× with EtOAc. The combined EtOAc layers were washed 2× with H$_2$O and dried over MgSO$_4$. After concentration under vacuum, the resulting residue was chromatographed on silica gel. Gradient elution CH$_2$Cl$_2$ to 10% MeOH/CH$_2$Cl$_2$ eluted the 1-(2-(4-nitrophenoxy)ethyl)pyrrolidine (560 mg) as an orange oil. Further purification employing reverse phase chromatography (MeOH/H$_2$O/0.1% TFA) yielded 413 mg of a yellow oil. Subsequent conversion of the aryl nitro substituent to the title aryl amine was accomplished following the procedure described in Example 6 step C. MS (ESI) 207 (M+H)$^+$.

Step B. Preparation of (4-(4-chlorophenyl)-N-(4-(2-(pyrrolidin-1-yl)ethoxy)phenyl)-1H-pyrrole-2-carboxamide 4-(2-(Pyrrolidin-1-yl)ethoxy)benzenamine (35 mg) from step A was converted to the title compound (26 mg) by acylation with 4-(4-chlorophenyl)-1H-pyrrole-2-carboxylic acid (25 mg) following the procedure described in step C of Example 1. Step C. MS (ESI) 410 (M+H)$^+$.

Step C. Preparation of 7-(4-chlorophenyl)-2-(4-(2-(pyrrolidin-1-yl)ethoxy)phenyl)-3,4-dihydropyrrolo[1,2-a]pyrazin-1(2H)-one trifluoroacetic acid salt Following the procedure described in Example 1 step D, the above product of step B (12 mg) was alkylated with 1,2-dibromoethane to yield 6.2 mg of the title compound. MS (ESI) 436 (M+H)$^+$.

Examples 9-13

These examples were prepared analogous to Example 7 using commercially available or prepared (via procedure described in *J. Med. Chem.* 2005, 48, 1318) anilines -continued

| Example # | Structure | MS(ESI) (M + H)+ |
|---|---|---|
| 11 | 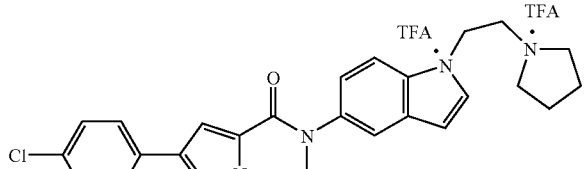 | 459 |
| 12 | 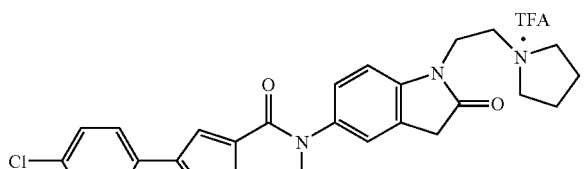 | 477 |
| 13 | 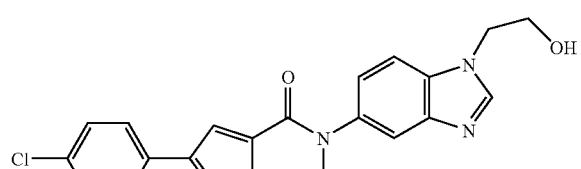 | 407 |

Example 14

Preparation of 7-(4-chlorophenyl)-2-(4-methoxy-3-(2-(pyrrolidin-1-yl)ethoxy)phenyl)-3,4-dihydropyrrolo[1,2-a]pyrazin-1(2H)-one trifluoroacetic acid salt

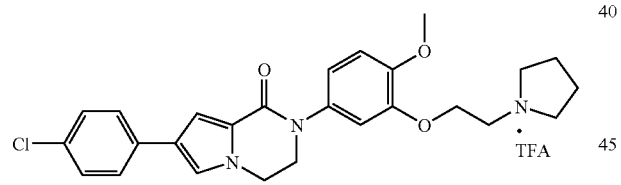

Step A. Preparation of 4-methoxy-3-(2-(pyrrolidin-1-yl)ethoxy)benzenamine

A stirred DMF suspension (5 mL) of 2-methoxy-5-nitrophenol (0.5 g, 2.96 mmol), 1-(2-chloroethyl)pyrrolidine hydrochloride (0.75 g (4.43 mmol) and $K_2CO_3$ (1.02 g, 7.4 mmol) was heated at 80° C. for 2 hr. After cooling to RT, the reaction was diluted with 20 mL of $H_2O$ and extracted with EtOAc (3×20 mL). The combined EtOAc layers were washed brine and dried over $MgSO_4$. After concentration under vacuum, the resulting residue was chromatographed on silica gel. Gradient elution $CH_2Cl_2$ to 10% MeOH/$CH_2Cl_2$ eluted N-(2-(2-methoxy-5-nitrophenoxy)ethyl)pyrrolidine (507 mg) as a light orange solid. Subsequent conversion of the aryl nitro substituent to the title aryl amine was accomplished in 87% yield following the procedure described in step C of Example 6. MS (ESI) 237 (M+H)+.

Step B. Preparation of 4-(4-chlorophenyl)-N-(4-methoxy-3-(2-(pyrrolidin-1-yl)ethoxy)phenyl)-1H-pyrrole-2-carboxamide Acylation of 4-methoxy-3-(2-(pyrrolidin-1-yl)ethoxy)benzenamine from step A with 4-(4-chlorophenyl)-1H-pyrrole-2-carboxylic acid to generate the title compound in 74% yield was achieved via the procedure described in step C of Example 1. MS (ESI) 440 (M+H)+.

Step C. Preparation of 7-(4-chlorophenyl)-2-(4-methoxy-3-(2-(pyrrolidin-1-yl)ethoxy)phenyl)-3,4-dihydropyrrolo[1,2-a]pyrazin-1(2H)-one trifluoroacetic acid salt Following the procedure described in Example 1 step D, the product of step B (30 mg) was alkylated with 1,2-dibromoethane to yield 23 mg of the title compound. MS (ESI) 466 (M+H)+.

Example 15

Preparation of 2-(3-chloro-4-(2-(pyrrolidin-1-yl)ethoxy)phenyl)-7-(4-chlorophenyl)-3,4-dihydropyrrolo[1,2-a]pyrazin-1(2H)-one trifluoroacetic acid salt

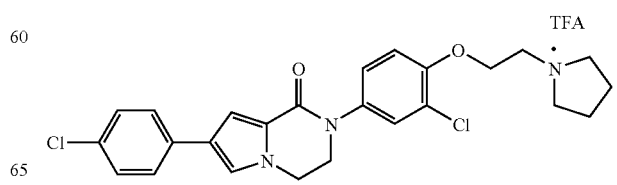

Step A. Preparation of 1-(2-(2-chloro-4-nitrophenoxy)ethyl)pyrrolidine

A suspension of Cs$_2$CO$_3$ (23.1 g, 71.0 mmol), 1-(2-chloroethyl)pyrrolidine, hydrochloride (9.0 g, 53.2 mmol) and 2-chloro-4-nitrophenol (3.0 g, 17.8 mmol) in DMF (50 mL) was heated at 80° C. for 4 days. After dilution with H$_2$O (50 mL), the mixture was extracted with EtOAc (2×100 mL). The combined organic layers were washed with H$_2$O (30 mL), then with brine prior to drying over MgSO$_4$. After removal of the solvent under vacuum, the residue was chromatographed on silica gel using 5%-10% gradient MeOH/CH$_2$Cl$_2$ to yield yellow brownish solid (1.5 g, 31%) MS (ESI) 271 (M+H)$^+$.

Step B. Preparation of 3-chloro-4-(2-(pyrrolidin-1-yl)ethoxy)benzenamine

A suspension of Zn powder (620 mg, 9.48 mmol) and 1-(2-(2-chloro-4-nitrophenoxy)ethyl)pyrrolidine (320 mg, 1.19 mmol) in AcOH:H$_2$O (3:1 mL) was heated at 55° C. for 2 h. After cooling the reaction to RT, any solid was removed by filtration and rinsed with AcOH and CH$_2$Cl$_2$. Once the combined filtrate was concentrated using a rotavap, the resulting residue was adjusted pH to 10 with NH$_4$OH and extracted with CH$_2$Cl$_2$ (2×50 mL). The combined organic layers were washed with H$_2$O (10 mL), then dried over MgSO$_4$. After removal of the solvent under vacuum the pale brownish oil (0.26 g, 93%) was carried forward without further purification. MS (ESI) 241 (M+H)$^+$.

Step C. Preparation N-(3-chloro-4-(2-(pyrrolidin-1-yl)ethoxy)phenyl)-4-(4-chlorophenyl)-1H-pyrrole-2-carboxamide 3-Chloro-4-(2-(pyrrolidin-1-yl)ethoxy)benzenamine was converted to the title compound (20 mg) by acylation with 4-(4-chlorophenyl)-1H-pyrrole-2-carboxylic acid following the procedure described in step C of Example 1. MS (ESI) 444 (M+H)$^+$.

Step D. Preparation of 2-(3-chloro-4-(2-(pyrrolidin-1-yl)ethoxy)phenyl)-7-(4-chlorophenyl)-3,4-dihydropyrrolo[1,2-a]pyrazin-1(2H)-one trifluoroacetic acid salt Following the procedure described in Example 1 step D, the above product of step C (20 mg) was alkylated with 1,2-dibromoethane to yield 10 mg of the title compound. MS (ESI) 470 (M+H)$^+$.

Example 16

Preparation of 7-(4-chlorophenyl)-2-(3-methoxy-4-(3-(pyrrolidin-1-yl)propoxy)phenyl)-3,4-dihydropyrrolo[1,2-a]pyrazin-1(2H)-one trifluoroacetic acid salt

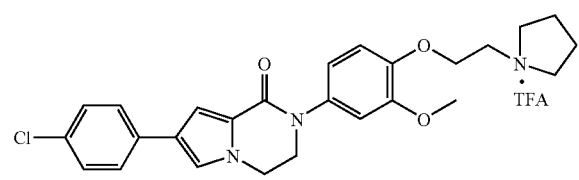

Step A. Preparation of 1-(3-bromopropoxy)-2-methoxy-4-nitrobenzene

A suspension of K$_2$CO$_3$ (2.0 g, 14.5 mmol), dibromopropane (8.8 g, 43.4 mmol) and the potassium salt of 2-methoxy-4-nitrophenol (3.0 g, 14.5 mmol) in DMF (50 mL) was heated at 80° C. for 24 hr. After removal of any precipitate by filtration, the filtrate was partitioned between EtOAc/H$_2$O (100/20 mL). The organic layer was washed with brine and dried over MgSO$_4$. After removal of the solvent under vacuum, the residue was chromatographed on silica gel using 5%-20% gradient EtOAc/hexanes to elute the title compound as a yellow brownish solid (1.5 g, 36%) MS (ESI) 292 (M+H)$^+$.

Step B. Preparation of a mixture of 1-(3-(2-methoxy-4-nitrophenoxy)propyl)pyrrolidine and 1-(2-methoxy-4-nitrophenyl)pyrrolidine A mixture of 1-(3-bromopropoxy)-2-methoxy-4-nitrobenzene (250 mg, 0.86 mmol) from step A and pyrrolidine (613 mg, 8.6 mmol) in isopropanol (2 mL) was heated at 80° C. for 24 h. After being concentrated under reduced pressure, the residue was diluted in EtOAc (50 mL) and washed with H$_2$O (2×5 mL) prior to drying the organic layer over Na$_2$SO$_4$. Following solvent removal under vacuum, the resulting yellow reddish oil (0.20 g, 83%) comprising a 1:1 mixture of 1-(3-(2-methoxy-4-nitrophenoxy)propyl)pyrrolidine and 1-(2-methoxy-4-nitrophenyl)pyrrolidine was carried forward without further purification. MS (ESI) 281 and 223 (M+H)$^+$.

Step C. Preparation of a mixture of 3-methoxy-4-(3-(pyrrolidin-1-yl)propoxy)benzenamine and 3-methoxy-4-(pyrrolidin-1-yl)benzenamine A mixture of 1-(3-(2-methoxy-4-nitrophenoxy)propyl)pyrrolidine and 1-(2-methoxy-4-nitrophenyl)pyrrolidine (150 mg, 0.53 mmol) prepared in step B and 15 mg of 5% Pd/C in MeOH (3 mL) was stirred under 1 atm of H$_2$ for 2 h. The reaction was filtered through celite and concentrated to yield the corresponding mixture of anilines (110 mg). MS (ESI) 251 and 193 (M+H)$^+$.

Step D. Preparation of a Mixture of 4-(4-chlorophenyl)-N-(3-methoxy-4-(3-(pyrrolidin-1-yl)propoxy)phenyl)-1H-pyrrole-2-carboxamide and 4-(4-chlorophenyl)-N-(3-methoxy-4-(pyrrolidin-1-yl)phenyl)-1H-pyrrole-2-carboxamide The above mixture of 3-methoxy-4-(3-(pyrrolidin-1-yl)propoxy)benzenamine and 3-methoxy-4-(pyrrolidin-1-yl)benzenamine were converted to the title compounds (30 mg) by acylation with 4-(4-chlorophenyl)-1H-pyrrole-2-carboxylic acid (25 mg) following the procedure described in step C of Example 1. MS (ESI) 396 (M+H)$^+$; MS (ESI) 454 (M+H)$^-$.

Step E. Preparation of 7-(4-chlorophenyl)-2-(3-methoxy-4-(3-(pyrrolidin-1-yl)propoxy)phenyl)-3,4-dihydropyrrolo[1,2-a]pyrazin-1(2H)-one trifluoroacetic acid salt Following the procedure described in Example 1 step D, the above mixture of anilides of step D (24 mg) was alkylated with 1,2-dibromoethane to yield a corresponding mixture of pyrazinone products. Preparative reverse phase chromatography (C18 YMC column employing a gradient elution with H$_2$O/MeOH containing 0.1% TFA eluted 5 mg of the title compound. MS (ESI) 480 (M+H)$^+$.

Example 17

Preparation of 7-(4-chlorophenyl)-2-(3-methoxy-4-(pyrrolidin-1-yl)phenyl)-3,4-dihydropyrrolo[1,2-a]pyrazin-1(2H)-one trifluoroacetic acid salt

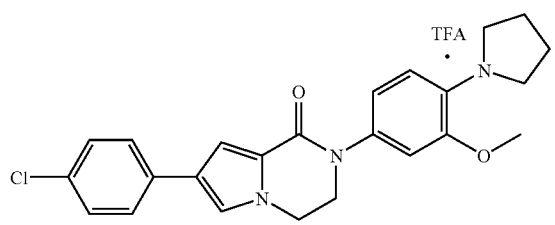

Step A. Preparation of 7-(4-chlorophenyl)-2-(3-methoxy-4-(pyrrolidin-1-yl)phenyl)-3,4-dihydropyrrolo[1,2-a]pyrazin-1(2H)-one trifluoroacetic acid salt The title compound (12 mg) was obtained from the mixture of pyrazinones described in step D of Example 16 by preparative reverse phase chromatography (C18 YMC column employing a gradient elution with H$_2$O/MeOH containing 0.1% TFA. MS (ESI) 422 (M+H)$^-$.

Example 18

Preparation of tert-butyl 2-(4-(7-(4-chlorophenyl)-1-oxo-3,4-dihydropyrrolo[1,2-a]pyrazin-2(1H)-yl)-2-methoxyphenoxy)ethylcarbamate

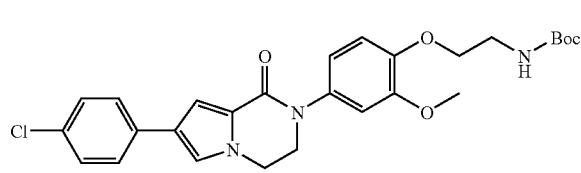

Step A. Preparation of tert-butyl 2-(4-amino-2-methoxyphenoxy)ethylcarbamate A suspension of K$_2$CO$_3$ (280 mg, 2 mmol), NaI (700 mg, 5 mmol), the potassium salt of 2-methoxy-4-nitrophenol (1.37 g, 6.6 mmol), and t-butyl 2-chloroethylcarbamate (1.4 g, 8 mmol) in DMF (8 mL) was heated at 90° C. for 6 hr. After dilution with H$_2$O, the mixture was extracted 4× with CH$_2$Cl$_2$. The combined organic layers were washed 2× with aq. K$_2$CO$_3$, then with brine prior to drying over Na$_2$SO$_4$. After removal of the solvent under vacuum, the residue was chromatographed on silica gel using 5% EtOAc/CH$_2$Cl$_2$ to elute 870 mg of nitrophenyl ether. Pd catalyzed reduction in ethanol as described in step C of Example 6 yielded tert-butyl 2-(4-amino-2-methoxyphenoxy)ethylcarbamate (700 mg) as an off white solid which was carried forward without further purification.

Step B. Preparation tert-butyl 2-(4-(3-(4-chlorophenyl)-1H-pyrrole-5-carboxamido)-2-methoxyphenoxy)ethylcarbamate tert-Butyl-(4-amino-2-methoxyphenoxy)ethylcarbamate was converted to the title compound (80 mg) by acylation with 4-(4-chlorophenyl)-1H-pyrrole-2-carboxylic acid (25 mg) following the procedure described in step C of Example 1. MS (ESI) 386 (M-Boc)$^+$.

Step C. Preparation of tert-butyl 2-(4-(7-(4-chlorophenyl)-1-oxo-3,4-dihydropyrrolo[1,2-a]pyrazin-2(1H)-yl)-2-methoxyphenoxy)ethylcarbamate Following the procedure described in step D of Example 1, the above product of step B (55 mg) was alkylated with 1,2-dibromoethane to yield 7 mg of the title compound. MS (ESI) 456 (M+H)$^+$.

Example 19

Preparation of 7-(4-chlorophenyl)-2-(3-methoxy-4-(1H-1,2,4-triazol-1-yl)phenyl)-3,4-dihydropyrrolo[1,2-a]pyrazin-1(2H)-one

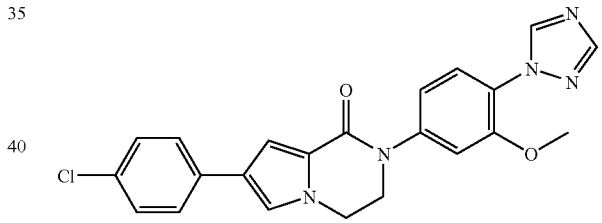

Step A. Preparation of 4-(4-chlorophenyl)-N-(3-methoxy-4-(1H-1,2,4-triazol-1-yl)phenyl)-1H-pyrrole-2-carboxamide 3-Methoxy-4-(1H-1,2,4-triazol-1-yl)benzenamine, prepared as described in Bioorg. Med. Chem. Lett. 2003, 13, 2059, was converted to the title compound (45 mg) by acylation with 4-(4-chlorophenyl)-1H-pyrrole-2-carboxylic acid (30 mg) following the procedure described in step C of Example 1. MS (ESI) 394 (M+H)$^+$.

Step B. Preparation of 7-(4-chlorophenyl)-2-(3-methoxy-4-(1H-1,2,4-triazol-1-yl)phenyl)-3,4-dihydropyrrolo[1,2-a]pyrazin-1(2H)-one Following the procedure described in step D of Example 1, the above product of step B (45 mg) was alkylated with 1,2-dibromoethane to yield 19 mg of the title compound. MS (ESI) 420 (M+H)$^+$.

Example 20

Preparation of (R)-7-(4-chlorophenyl)-2-(4-(3-hydroxypyrrolidin-1-yl)-3-methoxyphenyl)-3,4-dihydropyrrolo[1,2-a]pyrazin-1(2H)-one trifluoroacetic acid salt

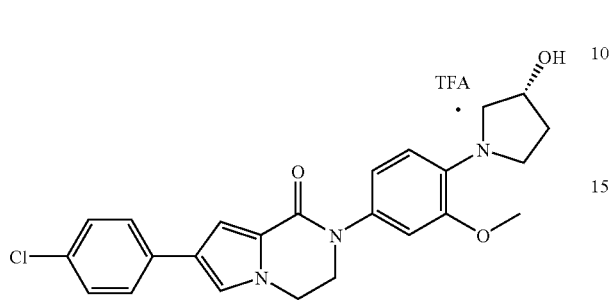

Step A. Preparation of (R)-4-(4-chlorophenyl)-N-(4-(3-hydroxypyrrolidin-1-yl)-3-methoxyphenyl)-1H-pyrrole-2-carboxamide (R)-1-(4-amino-2-methoxyphenyl)pyrrolidin-3-ol, preparation described in Patent WO 2005/042541, was converted to the title compound (48 mg) by acylation with 4-(4-chlorophenyl)-1H-pyrrole-2-carboxylic acid (30 mg) following the procedure described in step C of Example 1. MS (ESI) 412 (M+H)+.

Step B. Preparation of (R)-7-(4-chlorophenyl)-2-(4-(3-hydroxypyrrolidin-1-yl)-3-methoxyphenyl)-3,4-dihydropyrrolo[1,2-a]pyrazin-1(2H)-one trifluoroacetic acid salt Following the procedure described in step D of Example 1, the above product of step A (48 mg) was alkylated with 1,2-dibromoethane to yield 16 mg of the title compound. MS (ESI) 438 (M+H)+.

Example 21

Preparation of 7-(4-chlorophenyl)-2-(3-methoxy-4-(2-(amino)ethoxy)phenyl)-3,4-dihydropyrrolo[1,2-a]pyrazin-1(2H)-one hydrochloric acid salt

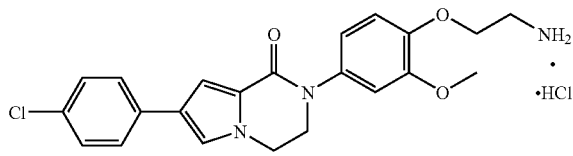

The title compound (6.1 mg) was obtained by stirring a solution of tert-butyl 2-(4-(7-(4-chlorophenyl)-1-oxo-3,4-dihydropyrrolo[1,2-a]pyrazin-2(1H)-yl)-2-methoxyphenoxy)ethylcarbamate (7.0 mg, 0.0136 mmol), preparation described in step D of Example 15, in 4 N HCl in 1,4-dioxane (0.27 ml, 1.08 mmol) for 20 min and subsequent removal of the volatiles under vacuum. MS (ESI) 421 (M+H)+.

Example 22

Preparation of 7-(4-chlorophenyl)-2-(3,4-dimethoxyphenyl)-3,4-dihydropyrrolo[1,2-a]pyrazin-1(2H)-one

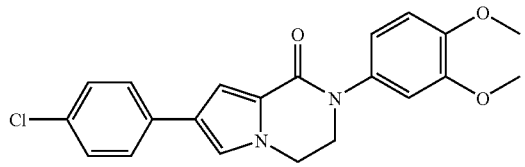

Step A. Preparation of 4-bromo-N-(3,4-dimethoxyphenyl)-1H-pyrrole-2-carboxamide 3,4-dimethoxyaniline was converted to the title compound in 97% yield following the procedure described in step B of Example 2. MS (ESI) 325, 327 (M+H)+.

Step B. Preparation of 7-bromo-2-(3,4-dimethoxyphenyl)-3,4-dihydropyrrolo[1,2-a]pyrazin-1(2H)-one Following the procedure described in Example 1 step D, the product of step A (140 mg) was alkylated with 1,2-dibromoethane to yield 143 mg of the title compound. MS (ESI) 351, 353 (M+H)−.

Step C. Preparation of 7-(4-chlorophenyl)-2-(3,4-dimethoxyphenyl)-3,4-dihydropyrrolo[1,2-a]pyrazin-1(2H)-one Following the procedure described in step A of Example 1, the product of step B (50 mg) was converted to the title compound in (10 mg). MS (ESI) 383 (M+H)+.

Example 23

Preparation of 2-(4-(2-(1H-pyrrol-1-yl)ethoxy)-3-methoxyphenyl)-7-(4-chlorophenyl)-3,4-dihydropyrrolo[1,2-a]pyrazin-1(2H)-one trifluoroacetic acid

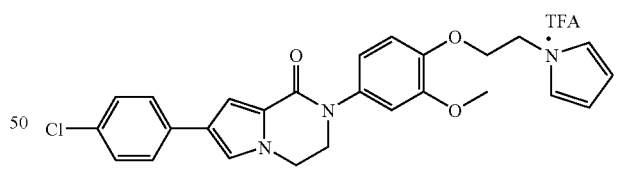

Step A. Preparation of 4-(2-(1H-pyrrol-1-yl)ethoxy)-3-methoxyaniline

Following procedure described in step A of Example 18, the title compound was prepared from the potassium salt of 2-methoxy-4-nitrophenol and 1-(2-bromoethyl)-1H-pyrrole in 76% yield. MS (ESI) 233 (M+H)+.

Step B. Preparation 4-(4-chlorophenyl)-N-(4-methoxy-3-(2-(pyrrolidin-1-yl)ethoxy)phenyl)-1H-pyrrole-2-carboxamide Acylation of 4-(2-(1H-pyrrol-1-yl)ethoxy)-3-methoxyaniline from step A with 4-(4-chlorophenyl)-1H-pyrrole-2- carboxylic acid to generate the title compound in 85% yield was achieved via the procedure described in step C of Example 1. MS (ESI) 436 (M+H)+.

Step C. Preparation of 2-(4-(2-(1H-pyrrol-1-yl)ethoxy)-3-methoxyphenyl)-7-(4-chlorophenyl)-3,4-dihydropyrrolo[1,2-a]pyrazin-1(2H)-one trifluoroacetic acid Following the procedure described in Example 1 step D, the product of step B (50 mg) was alkylated with 1,2-dibromoethane to yield 5.0 mg of the title compound. MS (ESI) 462 (M+H)+.

Example 24

Preparation of 7-(4-chlorophenyl)-2-(3-methoxy-4-(2-(tetrahydrofuran-2-yl)ethoxy)phenyl)-3,4-dihydropyrrolo[1,2-a]pyrazin-1(2H)-one

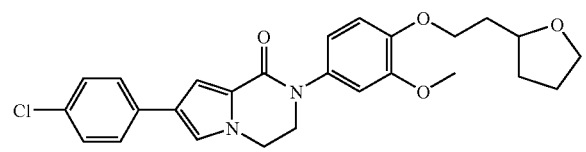

Step A. Preparation of 3-methoxy-4-(2-(tetrahydrofuran-2-yl)ethoxy)aniline

To a solution of 2-(tetrahydrofuran-2-yl)ethanol (1.0 g, 8.61 mmol), prepared following the procedure as described in *Synthesis* 1996, 594, in 15 mL of DMSO was added NaH (344 mg, 8.61 mmol, 60% in mineral oil) in portions. After the resulting suspension was stirred for 15 min., a solution of 1-chloro-2-methoxy-4-nitrobenzene in 5 mL of DMSO was added dropwise. The reaction mixture was stirred overnight, quenched with 15 mL of H$_2$O, and extracted with EtOAc (3×30 mL). The organic layers were combined, dried over Na$_2$SO$_4$, and conc. in vacuo to yield a brown oil. The oil was purified by column chromatography (silica gel, 0%-35% gradient elution with EtOAc/hexanes) to yield 1.68 g (73%) of 2-(2-(2-methoxy-4-nitrophenoxy)ethyl)tetrahydrofuran as a yellow solid. MS (ESI) 268 (M+H)+. Subsequent conversion of the aryl nitro substituent to the title aryl amine was accomplished in 98% yield, following the procedure described in Example 6 step C. MS (ESI) 238 (M+H)+.

Step B. Preparation of 4-(4-chlorophenyl)-N-(3-methoxy-4-(2-(tetrahydrofuran-2-yl)ethoxy)phenyl)-1H-pyrrole-2-carboxamide Acylation of 3-methoxy-4-(2-(tetrahydrofuran-2-yl)ethoxy)aniline from step A with 4-(4-chlorophenyl)-1H-pyrrole-2-carboxylic acid to generate the title compound in 98% yield was achieved via the procedure described in step C of Example 1. The crude product was used for next step without further purification.

Step C. Preparation of 7-(4-chlorophenyl)-2-(3-methoxy-4-(2-(tetrahydrofuran-2-yl)ethoxy)phenyl)-3,4-dihydropyrrolo[1,2-a]pyrazin-1(2H)-one Following the procedure described in Example 1 step D, the product of step B (120 mg) was alkylated with 1,2-dibromoethane to yield 20 mg of the title compound. MS (ESI) 467 (M+H)+.

Example 25

Preparation of 7-(4-chlorophenyl)-2-(4-(3-hydroxy-3-methylbutoxy)-3-methoxyphenyl)-3,4-dihydropyrrolo[1,2-a]pyrazin-1(2H)-one

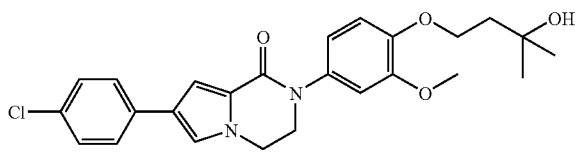

Step A. Preparation of 4-(4-amino-2-methoxyphenoxy)-2-methylbutan-2-ol 3-methylbutane-1,3-diol was converted to the title compound in 90% yield following the procedure described in step A of Example 24. MS (ESI) 226 (M+H)+.

Step B. Preparation of 4-(4-chlorophenyl)-N-(4-(3-hydroxy-3-methylbutoxy)-3-methoxyphenyl)-1H-pyrrole-2-carboxamide Acylation of 4-(4-amino-2-methoxyphenoxy)-2-methylbutan-2-ol from step A with 4-(4-chlorophenyl)-1H-pyrrole-2-carboxylic acid to generate the title compound was achieved via the procedure described in step C of Example 1. The crude product was used for next step without further purification.

Step C. Preparation of 7-(4-chlorophenyl)-2-(4-(3-hydroxy-3-methylbutoxy)-3-methoxyphenyl)-3,4-dihydropyrrolo[1,2-a]pyrazin-1(2H)-one Following the procedure described in Example 1 step D, the product of step B (120 mg) was alkylated with 1,2-dibromoethane to yield 15 mg of the title compound. MS (ESI) 455 (M+H)+.

Examples 26-28

Step A. Preparation of 1-(2-bromoethoxy)-2-methoxy-4-nitrobenzene

A mixture of the potassium salt of 2-methoxy-4-nitrophenol (2.07 g, 10.0 mmol), 1,2-dibromoethane (1.72 mL, 20.0 mol), 1 N KOH (50 mL), tetrabutyl ammonium bromide (3.22 g 10.0 mol), and CH$_2$Cl$_2$ was stirred overnight. The reaction was diluted with 300 mL of EtOAc, washed with sat. NH$_4$Cl solution (2×50 mL). The organic layer was dried over Na$_2$SO$_4$ prior to concentration in vacuum to a yellow solid. The solid was then washed with MeOH (2×5 mL) to yield 2.0 g (72%) of the title compound as a white solid. MS (ESI) 276, 278 (M+H)+.

Step B-E. Preparation of Example 26-28

These examples were prepared analogous to Example 16 using commercially available substituted pyrrolidines.

| Example # | Structure | MS(ESI) (M + H)+ |
|---|---|---|
| 26 | ![structure with TFA, ...''OH] | 482 |
| 27 | ![structure with TFA, OH] | 482 |
| 28 | ![structure with TFA, F F] | 502 |

Example 29

Preparation of 7-(4-chlorophenyl)-2-(3-methoxy-4-(2-(pyrrolidin-1-yl)ethoxy)phenyl)pyrrolo[1,2-a]pyrazin-1(2H)-one trifluoroacetic acid salt

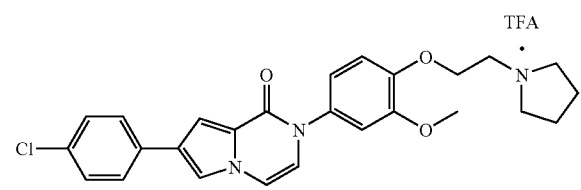

Step A. Preparation of N-((1,3-dioxolan-2-yl)methyl)-3-methoxy-4-(2-(pyrrolidin-1-yl)ethoxy)aniline A suspension of K$_2$CO$_3$ (235 mg, 1.70 mmol), 2-(bromomethyl)-1,3-dioxolane (400 mg, 1.70 mmol), and 3-methoxy-4-(2-(pyrrolidin-1-yl)ethoxy)benzenamine (3.0 g, 14.5 mmol), preparation described in Patent: WO2002/101146, in DMSO (17 mL) was heated at 80° C. for 24 hr. After removal of any precipitate by filtration, the filtrate was partitioned between EtOAc/H$_2$O (100/20 mL). The organic layer was washed with brine and dried over MgSO$_4$. After removal of the solvent under vacuum, the residue was chromatographed on silica gel using 0%-20% gradient EtOAc/Hexanes to elute the title compound as a yellow brownish oil (150 mg, 27%) MS (ESI) 323 (M+H)$^+$.

Step B. Preparation of 4-(4-chlorophenyl)-N-(2,2-dimethoxyethyl)-N-(3-methoxy-4-(2-(pyrrolidin-1-yl)ethoxy)phenyl)-1H-pyrrole-2-carboxamide To a stirring suspension of 4-(4-chlorophenyl)-1H-pyrrole-2-carboxylic acid (30 mg, 0.13 mmol), prepared in step A of Example 1, and a drop of DMF in 1.0 mL of CH$_2$Cl$_2$ was added 2 M oxalyl chloride solution in CH$_2$Cl$_2$ (0.081 mL, 0.16 mmol) dropwise over 5 min. After 30 min. stirring, the reaction was concentrated to give the corresponding acid chloride as a yellow oil which was dissolved in 1.0 mL of CH$_2$Cl$_2$. To the above solution was added a solution of N-((1,3-dioxolan-2-yl)methyl)-3-methoxy-4-(2-(pyrrolidin-1-yl)ethoxy)aniline in 0.5 mL of CH$_2$Cl$_2$. The reaction was stirred for 10 min. quenched with 1.0 mL of sat. NaHCO$_3$ solution, extracted with EtOAc (3×15 mL). The combined EtOAc solutions were washed with brine, dried over Na$_2$SO$_4$, and conc. in vacuo to yield a brown oil. The oil was purified by column chromatography (silica gel, 0%-20% gradient elution with MeOH/CH$_2$Cl$_2$) to yield 42 mg (61%) of title compound as a yellow oil. MS (ESI) 526 (M+H)$^+$.

Step C. Preparation of a mixture of 4-(4-chlorophenyl)-N-(3-methoxy-4-(2-(pyrrolidin-1-yl)ethoxy)phenyl)-N-(2-oxoethyl)-1H-pyrrole-2-carboxamide and 7-(4-chlorophenyl)-4-hydroxy-2-(3-methoxy-4-(2-(pyrrolidin-1-yl)ethoxy)phenyl)-3,4-dihydropyrrolo[1,2-a]pyrazin-1(2H)-one A mixture of 4-(4-chlorophenyl)-N-(2,2-dimethoxyethyl)-N-(3-methoxy-4-(2-(pyrrolidin-1-yl)ethoxy)phenyl)-1H-pyrrole-2-carboxamide (40 mg, 0.076 mmol) prepared in step B, 1 drop of H$_2$O, and PTSA H$_2$O (1.4 mg. 00076 mmol) in acetone (1.0 mL) was refluxed overnight. The reaction was diluted in Et₂O (20 mL) and washed with sat. NaHCO₃ (2×5 mL) prior to drying the organic layer over Na₂SO₄. Following solvent removal under vacuum, the resulting oil (0.20 g, 83%) comprising a 8:1 mixture of title compounds which was carried forward without further purification.

Step D. Preparation of 7-(4-chlorophenyl)-2-(3-methoxy-4-(2-(pyrrolidin-1-yl)ethoxy)phenyl)pyrrolo[1,2-a]pyrazin-1(2H)-one trifluoroacetic acid salt The above mixture from step C was dissolved in 0.75 mL of CH₃SO₃H and heated to 45° C. After stirring 2 days, the reaction was cooled down to rt and then slowly poured into ice-sat. NaHCO3 solution mixture. The resultant mixture was extracted with EtOAc (3×10 mL). The combined EtOAc solutions were washed with brine, dried over Na₂SO₄, and concentrated in vacuum to a brown oil which was purified by prep reverse phase HPLC (Phenomenex Luna 5u C18 21.2×100, H₂O/MeOH/0.1% TFA) to yield 19 mg (43%) of the title compound as a white lyophilate. MS (ESI) 464 (M+H)⁺.

Example 30

Preparation of 7-(4-(4-Chlorophenoxy)phenyl)-2-(4-(2-hydroxy-2-methylpropoxy)-3-methoxyphenyl)-3,4-dihydropyrrolo[1,2-a]pyrazin-1(2H)-one

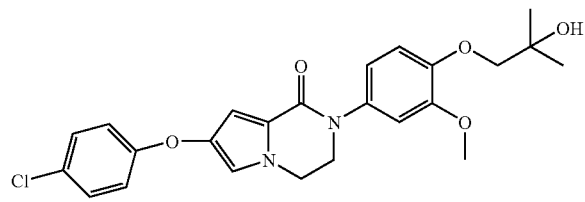

Step A. Preparation of 4-Bromo-N-(4-(2-hydroxy-2-methylpropoxy)-3-methoxyphenyl)-1H-pyrrole-2-carboxamide To a solution of 4-bromo-1H-pyrrole-2-carboxylic acid (1.00 g, 5.30 mmol), preparation described in step A of Example 2, and 1-(4-amino-2-methoxyphenoxy)-2-methylpropan-2-ol (1.12 g, 5.30 mmol), preparation described in step A of Example 4. in dichloroethane (46.0 mL) was added EDC (2.03 g, 10.6 mmol) and HOBT (1.62 g, 10.6 mmol) and the reaction was allowed to stir at rt for 16 h. The reaction mixture was diluted with EtOAc (100 mL), washed with sat. NaHCO₃ (3×100 mL), water, brine, dried over anhydrous Na₂SO₄ and concentrated to give 1.84 g of the title compound as a brown oil which was used in the next step without purification: HPLC a) column: Phenomenex Luna 5µ 4.6×50 mm, 4 min gradient, 10% MeOH/90% H₂O/0.1% H₃PO₄ to 90% MeOH/10% H₂O/0.1% H₃PO₄; 1 min hold, 4 mL/min UV detection at 220 nm, 3.058 min retention time, (91%); HPLC b) column: Phenomenex Luna C18 4.6×50 mm, 4 min gradient, 10% MeOH/90% H₂O/0.1% TFA to 90% MeOH/10% H₂O/0.1% TFA, 1 min hold; 4 mL/min, UV detection at 220 nm, 3.051 min retention time; MS (ES) 385 [M+H]⁺.

Step B. Preparation of 7-Bromo-2-(4-(2-hydroxy-2-methylpropoxy)-3-methoxyphenyl)-3,4-dihydropyrrolo[1,2-a]pyrazin-1(2H)-one A mixture of 4-bromo-N-(4-(2-hydroxy-2-methylpropoxy)-3-methoxyphenyl)-1H-pyrrole-2-carboxamide (1.50 g, 3.92 mmol), 1,2-dibromoethane (1.68 mL, 19.6 mmol), NBu₄Br (1.26 g, 3.93 mmol) and 1N NaOH (19.6 mL, 19.6 mmol) in dichloroethane (19.6 mL) was allowed to stir at 50° C. for 16 h. The reaction mixture was cooled to rt, diluted with EtOAc (150 mL), washed with water, brine, dried over anhydrous Na₂SO₄ and concentrated. To the resulting brown oil was triturated with EtOAc (25 mL) to give 643 mg of the title compound as a light gray solid: ¹H NMR (500 MHz, CDCl₃) δ 1.34 (s, 6H), 2.67 (br. s., 1H), 3.83 (s, 2H), 3.85 (s, 3H), 4.04-4.08 (m, 2H), 4.22-4.26 (m, 2H), 6.78 (t, J=5.5 Hz, 2H), 6.90-6.95 (m, 2H), 6.99 (s, 1H); HPLC a) column: Phenomenex Luna 5µ 4.6×50 mm, 4 min gradient, 10% MeOH/90% H₂O/0.1% H₃PO₄ to 90% MeOH/10% H₂O/0.1% H₃PO₄; 1 min hold, 4 mL/min UV detection at 220 nm, 2.730 min retention time, (99%); HPLC b) column: Phenomenex Luna C18 4.6×50 mm, 4 min gradient, 10% MeOH/90% H₂O/0.1% TFA to 90% MeOH/10% H₂O/0.1% TFA, 1 min hold; 4 mL/min, UV detection at 220 nm, 2.748 min retention time; MS (ES) 409 [M+H]⁺

Step C. Preparation of 7-(4-(4-Chlorophenoxy)phenyl)-2-(4-(2-hydroxy-2-methylpropoxy)-3-methoxyphenyl)-3,4-dihydropyrrolo[1,2-a]pyrazin-1(2H)-one A solution of 7-bromo-2-(4-(2-hydroxy-2-methylpropoxy)-3-methoxyphenyl)-3,4-dihydropyrrolo[1,2-a]pyrazin-1(2H)-one (50.0 mg, 0.123 mmol), 4-chlorophenol (24.0 mg, 0.185 mmol), CuI (2.3 mg, 0.0123 mmol), Cs₂CO₃ (80.2 mg, 0.246 mmol) and glycine methyl ester hydrochloride (5.15 mg, 0.0369 mmol) in degassed dioxane (0.300 mL) was stirred at 90° C. for 72 h. The mixture was cooled to rt, diluted with H₂O (5 mL) and extracted with EtOAc (×3, 15 mL). The combined organic layers were washed with brine, dried over Na₂SO₄, concentrated and purified by preparative HPLC: Phenomenex Luna AXIA 5µ C18 21.2×100 mm, 15 min gradient, 10% MeOH/90% H₂O/0.1% TFA to 90% MeOH/10% H₂O/0.1% TFA, 5 min hold; 20 mL/min, UV detection at 220 nm, 13.644 min retention time to afford 4.2 mg of the title compound as a tan solid: ¹H NMR (500 MHz, CDCl₃) δ 1.37 (s, 6H), 3.84 (s, 2H), 3.85 (s, 3H), 4.10-4.15 (m, 2H), 4.23-4.28 (m, 2H), 6.65 (s, 1H), 6.76 (d, J=2.2 Hz, 1H), 6.81 (dd, J=8.2, 2.2 Hz, 1H), 6.91-6.95 (m, 2H), 6.99 (d, J=9.3 Hz, 2H), 7.24-7.27 (m, 2H); HPLC a) column: Phenomenex Luna 5µ 4.6×50 mm, 4 min gradient, 10% MeOH/90% H₂O/0.1% H₃PO₄ to 90% MeOH/10% H₂O/0.1% H₃PO₄; 1 min hold, 4 mL/min UV detection at 220 nm, 3.443 min retention time, (>96%); HPLC b) column: Phenomenex Luna C18 4.6×50 mm, 4 min gradient, 10% MeOH/90% H₂O/0.1% TFA to 90% MeOH/10% H₂O/0.1% TFA, 1 min hold; 4 mL/min, UV detection at 220 nm, 3.433 min retention time; MS (ES) 457 [M+H]⁺.

Examples 31-40

Following the procedure described in step A of Example 1, these examples were prepared via a Suzuki coupling reaction between a commercially available aryl boronic acid and 7-Bromo-2-(4-(2-hydroxy-2-methylpropoxy)-3-methoxyphenyl)-3,4-dihydropyrrolo[1,2-a]pyrazin-1(2H)-one, preparation described in step B of Example 30.

| Example # | Stucture | MS(ESI) (M + H)+ |
|---|---|---|
| 31 | | 421 |
| 32 | | 435 |
| 33 | | 449 |
| 34 | | 435 |
| 35 | | 437 |
| 36 | | 491 |
| 37 | | 453 |

| Example # | Stucture | MS(ESI) (M + H)+ |
|---|---|---|
| 38 | | 425 |
| 39 | | 475 |
| 40 | | 457 |

Example 41

Preparation of 6-Bromo-7-(4-chlorophenyl)-2-(4-(2-hydroxy-2-methylpropoxy)-3-methoxyphenyl)-3,4-dihydropyrrolo[1,2-a]pyrazin-1(2H)-one

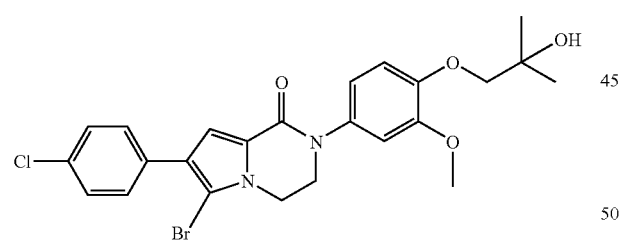

A solution of 7-bromo-2-(4-(2-hydroxy-2-methylpropoxy)-3-methoxyphenyl)-3,4-dihydropyrrolo[1,2-a]pyrazin-1(2H)-one (40.0 mg, 0.091 mmol) and NBS (16.7 mg, 0.094 mmol) in $CH_2Cl_2$ (0.90 mL) was stirred at rt for 10 min. The mixture was concentrated and purified by preparative HPLC: Phenomenex Luna AXIA 5μ C18 21.2×100 mm, 15 min gradient, 10% MeOH/90% $H_2O$/011% TFA to 90% MeOH/10% $H_2O$/0.1% TFA, 5 min hold; 20 mL/min, UV detection at 220 nm, 15.449 min retention time to afford 16.2 mg of the title compound as a colorless solid: $^1H$ NMR (500 MHz, $CDCl_3$) δ 1.35 (s, 6H), 3.84 (s, 2H), 3.86 (s, 3H), 4.10-4.16 (m, 2H), 4.25-4.32 (m, 2H), 6.81 (dd, J=8.5, 2.5 Hz, 1H), 6.94 (d, J=8.2 Hz, 1H), 6.96 (d, J=2.2 Hz, 1H), 7.21 (s, 1H), 7.38 (d, J=8.8 Hz, 2H), 7.53 (d, J=8.2 Hz, 2H); HPLC a) column: Phenomenex Luna 5μ 4.6×50 mm, 4 min gradient, 10% MeOH/90% $H_2O$/0.1% $H_3PO_4$ to 90% MeOH/10% $H_2O$/0.1% $H_3PO_4$; 1 min hold, 4 mL/min UV detection at 220 nm, 3.821 min retention time, (90%); HPLC b) column: Phenomenex Luna C18 4.6×50 mm, 4 min gradient, 10% MeOH/90% $H_2O$/0.1% TFA to 90% MeOH/10% $H_2O$/0.1% TFA, 1 min hold; 4 mL/min, UV detection at 220 nm, 3.811 min retention time; MS (ESI) 521 $[M+H]^+$.

Example 42

Preparation of 6-Chloro-7-(4-chlorophenyl)-2-(4-(2-hydroxy-2-methylpropoxy)-3-methoxyphenyl)-3,4-dihydropyrrolo[1,2-a]pyrazin-1(2H)-one

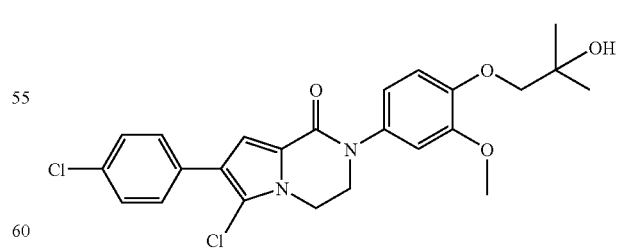

A solution of 7-bromo-2-(4-(2-hydroxy-2-methylpropoxy)-3-methoxyphenyl)-3,4-dihydropyrrolo[1,2-a]pyrazin-1(2H)-one (25.0 mg, 0.057 mmol) and NCS (11.71 mg, 0.088 mmol) in THF (0.440 mL) was stirred at rt for 18 h. The mixture was concentrated and purified by preparative HPLC: Phenomenex Luna AXIA 5μ C18 21.2×100 mm, 15 min gradient, 10% MeOH/90% H$_2$O/011% TFA to 90% MeOH/10% H$_2$O/0.1% TFA, 5 min hold; 20 mL/min, UV detection at 220 nm, 14.972 min retention time to afford 16.2 mg of the title compound as a colorless solid: $^1$H NMR (400 MHz, CDCl$_3$) δ 1.34 (s, 6H), 3.84 (s, 2H), 3.86 (s, 3H), 4.10-4.15 (m, 2H), 4.24-4.31 (m, 2H), 6.81 (dd, J=8.5, 2.5 Hz, 1H), 6.92-6.97 (m, 2H), 7.20 (s, 1H), 7.38 (d, J=8.2 Hz, 2H), 7.54 (d, J=8.2 Hz, 2H); HPLC a) column: Phenomenex Luna 5μ 4.6×50 mm, 4 min gradient, 10% MeOH/90% H$_2$O/0.1% H$_3$PO$_4$ to 90% MeOH/10% H$_2$O/0.1% H$_3$PO$_4$; 1 min hold, 4 mL/min UV detection at 220 nm, 3.801 min retention time, (85%); HPLC b) column: Phenomenex Luna C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 3.803 min retention time; MS (ES) 475 [M+H]$^+$.

Example 43

Preparation of 8-Bromo-7-(4-chlorophenyl)-2-(4-(2-hydroxy-2-methylpropoxy)-3-methoxyphenyl)-3,4-dihydropyrrolo[1,2-a]pyrazin-1(2H)-one

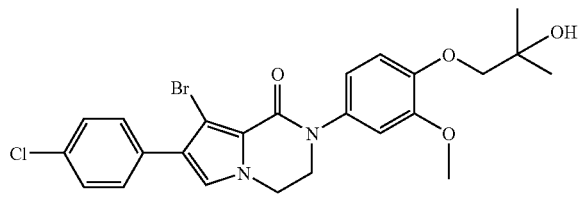

A −78° C. solution of 7-bromo-2-(4-(2-hydroxy-2-methylpropoxy)-3-methoxyphenyl)-3,4-dihydropyrrolo[1,2-a]pyrazin-1(2H)-one (30.0 mg, 0.068 mmol) in anhydrous THF (0.300 mL) was added dropwise to a −78° C. solution of s-BuLi (1.4 M in cyclohexanes, 0.150 mL, 0.211 mmol) and TMEDA (32 μL, 0.211 mmol). After stirring for 1 h at −78° C., Br$_2$ (3.5 mL, 0.068 mmol) was added. The resultant mixture was allowed to slowly warm to rt over a period of 3 h. The reaction was then quenched with sat. NH$_4$Cl, concentrated, extracted with CH$_2$Cl$_2$ (×3, 15 mL), dried over Na$_2$SO$_4$, concentrated and purified by preparative HPLC: Phenomenex Luna AXIA 5μ C18 21.2×100 mm, 25 min gradient, 10% MeOH/90% H$_2$O/01% TFA to 90% MeOH/10% H$_2$O/0.1% TFA, 5 min hold; 20 mL/min, UV detection at 220 nm, 20.210 min retention. This material was recrystallized using CH$_2$Cl$_2$/hexanes to afford 2.5 mg of the title compound as a light brown solid: $^1$H NMR (500 MHz, CDCl$_3$) δ 1.34 (s, 6H), 3.83 (s, 2H), 3.86 (s, 3H), 4.09-4.13 (m, 2H), 4.29-4.33 (m, 2H), 6.81 (dd, J=8.5, 2.5 Hz, 1H), 6.89-6.94 (m, 2H), 6.98 (d, J=2.2 Hz, 1H), 7.38 (d, J=8.2 Hz, 2H), 7.48(m, J=8.2 Hz, 2H); HPLC a) column: Phenomenex Luna 5μ 4.6×50 mm, 4 min gradient, 10% MeOH/90% H$_2$O/0.1% H$_3$PO$_4$ to 90% MeOH/10% H$_2$O/0.1% H$_3$PO$_4$; 1 min hold, 4 mL/min UV detection at 220 nm, 3.621 min retention time, (>90%); HPLC b) column: Phenomenex Luna C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 3.640 min retention time; MS (ES) 521 [M+H]$^+$.

Example 44

Preparation of 2-(4-(2-Hydroxy-2-methylpropoxy)-3-methoxyphenyl)-7-(phenethylthio)-3,4-dihydropyrrolo[1,2-a]pyrazin-1(2H)-one

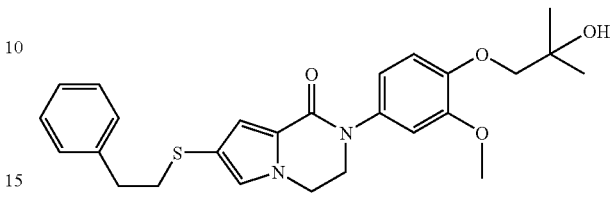

Step A. Preparation of methyl 4-(phenethylthio)-1H-pyrrole-2-carboxylate

A solution of sodium hydroxide (88.0 mg, 2.20 mmol) in degassed H$_2$O (0.500 mL) was added to a mixture of 2-methoxycarbonyl-4-thiocyanopyrrole (0.200 g, 1.10 mmol), prepared according to the procedure described in J. Chem. Soc. Perkin Trans. 2 1990, 699, and (2-bromoethyl)benzene (0.165 mL, 1.21 mmol) in degassed t-BuOH (2.0 mL). The reaction mixture was stirred at 60° C. for 2 h, cooled to rt and concentrated. The residue was dissolved in CH$_2$Cl$_2$ (50 mL) washed with H$_2$O (2×25 mL), dried over anhydrous Na$_2$SO$_4$, concentrated and purified by chromatography on silica gel with MeOH and CH$_2$Cl$_2$ (0-10% gradient) as the mobile phases to afford 0.247 g of the title compound as a light yellow oil: $^1$H NMR (500 MHz, CDCl$_3$) δ 2.83-2.88 (m, 2H), 2.89-2.95 (m, 2H), 3.87 (s, 3H), 6.94-6.97 (m, 1H), 7.00 (dd, J=2.7, 1.6 Hz, 1H), 7.14-7.22 (m, 3H), 7.26-7.30 (m, 2H), 9.30 (br. s., 1H); HPLC a) column: Phenomenex Luna 5μ 4.6×50 mm, 4 min gradient, 10% MeOH/90% H$_2$O/0.1% H$_3$PO$_4$ to 90% MeOH/10% H$_2$O/0.1% H$_3$PO$_4$; 1 min hold, 4 mL/min UV detection at 220 nm, 3.561 min retention time, (>95%); HPLC b) column: Phenomenex Luna C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 3.535 min retention time; MS (ES) 262 [M+H]$^+$.

Step B. Preparation of 4-(phenethylthio)-1H-pyrrole-2-carboxylic acid

A solution of methyl 4-(phenethylthio)-1H-pyrrole-2-carboxylate (233 mg, 0.890 mmol) and KOH (250 mg, 4.46 mmol) in MeOH (1.2 mL) and H$_2$O (0.6 mL) was stirred at 60° C. for 1.5 h, cooled to 0° C., acidified with concentrated HCl and diluted with H$_2$O. The solid precipitate was filtered, washed with H$_2$O and air dried under vacuum to afford the title compound (81.0 mg) as a colorless solid that was used in the next step without purification: $^1$H NMR (400 MHz, CDCl$_3$) δ 2.84-2.90 (m, 2H), 2.91-2.98 (m, 2H), 7.03-7.07 (m, 1H), 7.07-7.10 (m, 1H), 7.13-7.32 (m, 5H), 9.22 (br. s., 1 H); HPLC a) column: Phenomenex Luna 5μ 4.6×50 mm, 4 min gradient, 10% MeOH/90% H$_2$O/0.1% H$_3$PO$_4$ to 90% MeOH/10% H$_2$O/0.1% H$_3$PO$_4$; 1 min hold, 4 mL/min UV detection at 220 nm, 3.293 min retention time, (95%); HPLC b) column: Phenomenex Luna C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 3.258 min retention time; MS (ES): m/z 248.1 [M+H]$^+$.

Step C. Preparation of N-(4-(2-Hydroxy-2-methyl-propoxy)-3-methoxyphenyl)-4-(phenethylthio)-1H-pyrrole-2-carboxamide To a solution of 4-(phenethylthio)-1H-pyrrole-2-carboxylic acid (25.0 mg, 0.101 mmol) and 1-(4-amino-2-methoxyphenoxy)-2-methylpropan-2-ol (21.4 mg, 0.101 mmol) in dichloroethane (0.880 mL) was added EDC (38.8 mg, 0.202 mmol) and HOBT (30.9 mg, 0.202 mmol) and the reaction was allowed to stir at rt for 16 h. The reaction mixture was diluted with EtOAc (15 mL), washed with sat. NaHCO$_3$ (3×20 mL), water, brine, dried over anhydrous Na$_2$SO$_4$, concentrated and purified by preparative HPLC: Phenomenex Luna AXIA 5µ C18 21.2×100 mm, 15 min gradient, 10% MeOH/90% H$_2$O/0.1% TFA to 90% MeOH/10% H$_2$O/0.1% TFA, 5 min hold; 20 mL/min, UV detection at 220 nm, 10.739 min retention time to afford 21.3 mg of the title compound as brown solid: $^1$H NMR (500 MHz, CDCl$_3$) δ 1.34 (s, 6H), 2.85-2.97 (m, 4H), 3.81 (s, 2H), 3.85 (s, 3H), 6.67 (br. s., 1H), 6.88 (d, J=8.8 Hz, 1H), 6.95 (dd, J=8.8, 2.2 Hz, 1H), 7.02 (s, 1H), 7.15-7.23 (m, 3H), 7.24-7.32 (m, 2H), 7.37 (s, 1H), 7.55 (d, J=3.8 Hz, 1H), 9.83 (br. s., 1H);); HPLC a) column: Phenomenex Luna 5µ 4.6×50 mm, 4 min gradient, 10% MeOH/90% H$_2$O/0.1% H$_3$PO$_4$ to 90% MeOH/10% H$_2$O/0.1% H$_3$PO$_4$; 1 min hold, 4 mL/min UV detection at 220 nm, 3.650 min retention time, (>98%); HPLC b) column: Phenomenex Luna C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 3.660 min retention time; MS (ES) 441 [M+H]$^+$.

Step E. Preparation of 2-(4-(2-Hydroxy-2-methyl-propoxy)-3-methoxyphenyl)-7-(phenethylthio)-3,4-dihydropyrrolo[1,2-a]pyrazin-1(2H)-one A mixture of N-(4-(2-hydroxy-2-methylpropoxy)-3-methoxyphenyl)-4-(phenethylthio)-1H-pyrrole-2-carboxamide (20.0 mg, 0.0450 mmol), 1,2-dibromoethane (20.0 µL, 0.227 mmol), NBu$_4$Br (43.5 mg, 0.135 mmol) and 1N NaOH (0.227 mL, 0.227 mmol) in dichloroethane (0.227 mL) was allowed to stir at 50° C. for 4 h. The reaction mixture was cooled to rt, diluted with EtOAc (20 mL), washed with water (×2, 15 mL), brine, dried over anhydrous Na$_2$SO$_4$, concentrated and purified by preparative HPLC: Phenomenex Luna AXIA 5µ C18 21.2×100 mm, 15 min gradient, 10% MeOH/90% H$_2$O/0.1% TFA to 90% MeOH/10% H$_2$O/0.1% TFA, 5 min hold; 20 mL/min, UV detection at 220 nm, 8.949 min retention time to afford 11.5 mg of the title compound as a light yellow solid: $^1$H NMR (500 MHz, CDCl$_3$) δ 1.34 (s, 6H), 2.86-2.91 (m, 2H), 2.92-2.98 (m, 2H), 3.83 (s, 2H), 3.85 (s, 3H), 4.05-4.11 (m, 2H), 4.24-4.28 (m, 2H), 6.78-6.84 (m, 2H), 6.93 (d, J=8.2 Hz, 1H), 6.96 (d, J=2.2 Hz, 1H), 7.07 (s, 1H), 7.18 (d, J=8.2 Hz, 2H), 7.21 (d, J=7.1 Hz, 1H), 7.26-7.32 (m, 2H); HPLC a) column: Phenomenex Luna 5µ 4.6×50 mm, 4 min gradient, 10% MeOH/90% H$_2$O/011% H$_3$PO$_4$ to 90% MeOH/10% H$_2$O/0.1% H$_3$PO$_4$; 1 min hold, 4 mL/min UV detection at 220 nm, 3.470 min retention time, (>95%); HPLC b) column: Phenomenex Luna C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 3.461 min retention time; MS (ESI) 467 [M+H]$^-$.

Example 45

Preparation of 2-(4-(2-Hydroxy-2-methylpropoxy)-3-methoxyphenyl)-7-(phenylthio)-3,4-dihydropyrrolo[1,2-a]pyrazin-1(2H)-one

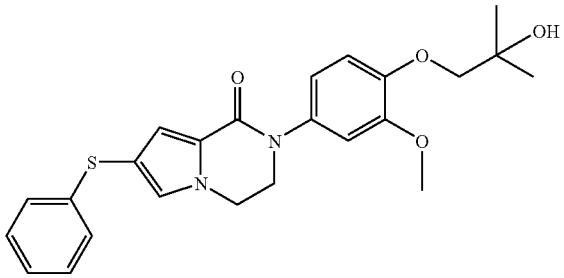

To a −78° C. solution of n-BuLi (1.6 M in hexanes, 77.0 µL, 0.123 mmol) in anhydrous THF (0.153 mL) was added a solution of 7-bromo-2-(4-(2-hydroxy-2-methylpropoxy)-3-methoxyphenyl)-3,4-dihydropyrrolo[1,2-a]pyrazin-1(2H)-one (50.0 mg, 0.123 mmol), prepared in step A of Example 30, in anhydrous THF (0.153 mL) dropwise over a period of 15 min. The reaction mixture was allowed to stir at −78° C. for 30 min at which point a solution of 1,2-diphenyldisulfane (16.1 mg, 0.073 mmol) in anhydrous THF (77.0 µL) was added dropwise. The reaction mixture was stirred at rt for 16 h, quenched with water (5 mL), extracted with ether (3×15 mL), dried over anhydrous Na$_2$SO$_4$, concentrated under reduced pressure and purified by preparative HPLC: Phenomenex Luna AXIA 5µ C18 21.2×100 mm, 15 min gradient, 10% MeOH/90% H$_2$O/0.1% TFA to 90% MeOH/10% H$_2$O/0.1% TFA, 5 min hold; 20 mL/min, UV detection at 220 nm, 12.716 min retention time to afford 2.2 mg of the title compound as a light yellow solid: $^1$H NMR (500 MHz, CDCl$_3$) δ 1.34 (s, 6H), 3.83 (s, 2H), 3.85 (s, 3H), 4.08-4.13 (m, 2H), 4.29-4.33 (m, 2H), 6.81 (dd, J=8.8, 2.2 Hz, 1H), 6.93 (d, J=8.8 Hz, 1H), 6.96 (d, J=3.3 Hz, 2H), 7.08-7.14 (m, 2H), 7.17-7.25 (m, 4H); HPLC a) column: Phenomenex Luna 5µ 4.6×50 mm, 4 min gradient, 10% MeOH/90% H$_2$O/0.1% H$_3$PO$_4$ to 90% MeOH/10% H$_2$O/0.1% H$_3$PO$_4$; 1 min hold, 4 mL/min UV detection at 220 nm, 3.283 min retention time, (>95%); HPLC b) column: Phenomenex Luna C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 3.300 min retention time; MS (ES) 439 [M+H]$^-$.

BIOLOGICAL EVALUATION

Radioligand Binding Assay for Assessment of MCHR1 Activity.

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl2, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC Unifilter plates pre-coated with 0.075 ml binding buffer containing 1% BSA, and washed 3 times with 0.4 ml of Phosphobuffered Saline (pH 7.4) containing 0.01% TX-100. Filters were dried, 0.05 ml microscint 20 was added to each well and radioactivity was subsequently quantified by scintillation counting on a TopCount™ microplate scintillation counter (Packard). Inhibitory constants were determined by nonlinear least squares analysis using a four parameter logistic equation.

UTILITIES AND COMBINATIONS

Utilities

The compounds of the present application can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease.

The compounds described in the present application could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present application include donepezil, tacrine, revastigraine, 5HT6, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

Combinations

The present application includes within its scope pharmaceutical compositions comprising, as an active ingredient, a therapeutically effective amount of at least one of the compounds of Formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the melanin-concentrating hormone receptor (MCHR) antagonists in accordance with the application.

Examples of suitable anti-obesity agents for use in combination with the compounds of the present application include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491, 134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present application include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594, 016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present application may be employed with a PPARα/γ dual agonist such as MK-767/KRP-297 (Merck/Kyorin; as described in, K. Yajima, et. al., *Am. J. Physiol. Endocrinol. Metab.,* 284: E966-E971 (2003)), AZ-242 (tesaglitazar; Astra-Zeneca; as described in B. Ljung, et. al., *J. Lipid Res.,* 43, 1855-1863 (2002)); muraglitazar; or the compounds described in U.S. Pat. No. 6,414,002.

The compounds of the present application may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.,* 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design,* 2, 1-40 (1996).

In addition, other squalene synthetase inhibitors suitable for use herein include the terpenoid pyrophosphates disclosed by P. Ortiz de Montellano, et al., *J. Med. Chem.,* 20, 243-249 (1977), the farnesyl diphosphate analog A and presqualene pyrophosphate (PSQ-PP) analogs as disclosed by Corey and Volante, *J. Am. Chem. Soc.,* 98, 1291-1293 (1976), phosphinylphosphonates reported by McClard, R. W. et al., *J. Am. Chem. Soc.,* 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future,* 24, 9-15 (1999), (Avasimibe); "The ACAT inhibitor, C1-1011 is effective in the prevention and regression of aortic fatty streak area in hamsters", Nicolosi et al., *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.,* 16 (1), 16-30 (1998); "RP 73163: a bioavailable alkylsulfinyl-diphenylimidazole ACAT inhibitor", Smith, C., et al., *Bioorg. Med. Chem. Lett,* 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways,* 173-98 (1995), Publisher: CRC, Boca Raton, Fla.; "ACAT inhibitors: potential anti-atherosclerotic agents", Sliskovic et al., *Curr. Med. Chem.,* 1 (3), 204-25 (1994); "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.,* 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na+/bile acid cotransporter inhibitor such as disclosed in Drugs of the Future, 24, 425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present application may be employed in combination with anti-hypertensive agents. Examples of suitable anti-hypertensive agents for use in combination with the compounds of the present application include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

It should be understood that while this application has been described herein in terms of specific embodiments set forth in detail, such embodiments are presented by way of illustration of the general principles of the application, and the application is not necessarily limited thereto. Certain modifications and variations in any given material, process step or chemical formula will be readily apparent to those skilled in the art without departing from the true spirit and scope of the present application, and all such modifications and variations should be considered within the scope of the claims that follow.

What is claimed is:

1. A compound of Formula I

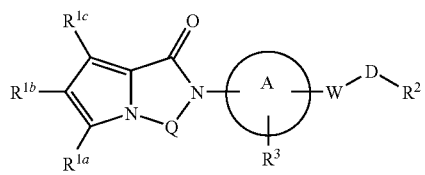

wherein
A is mono-cyclic aryl;
D is selected from the group consisting of a direct bond, alkyl, cycloalkyl and heterocyclyl;
Q is selected from the group consisting of $-(CR^8R^9)_n-$ and $-CR^8=CR^9-$;
W is selected from the group consisting of a direct bond, $-C(O)-$, $-O-$, $-N(R^{9a})-$, $-S(O)-$, $-S(O_2)-$, $-S(O_2)N(R^{9a})-$ and $-C(R^{10})(R^{11})-$;
$R^{1a}$, and $R^{1c}$ are independently selected from the group consisting of hydrogen, halo, aryl, aryloxy, arylthio, arylalkylthio, and heteroaryl, wherein aryl and heteroaryl, alone or as part of another group, may optionally and independently, be substituted with 1-3 $R^4$;
$R^{1b}$ is aryl which may be optionally substituted with 1-3 $R^4$;
$R^2$ is selected from the group consisting of hydroxyl, lower alkoxy, hydroxyalkyl, cycloalkoxy, OCONR$^7$R$^{7a}$, CN, CONR$^7$R$^{7a}$, SOR$^6$, SO$_2$R$^6$, NR$^7$COR$^{7b}$, NR$^7$CO$_2$R$^{7b}$, CO$_2$R$^6$, heterocyclyl, heteroaryl, NR$^7$R$^{7a}$, NR$^7$SO$_2$R$^6$ and COR$^6$;
$R^3$ is selected from the group consisting of hydrogen, hydroxyl, alkoxy, halo, CN, alkyl, perfluoroalkyl, cycloalkyl and cycloalkoxy, wherein $R^3$ and D may optionally be taken together with the atoms to which they are attached to form a 5 to 7-membered ring;
$R^4$ is selected from the group consisting of alkyl, halo, polyfluoroalkyl, alkoxy, polyfluoroalkyloxy, CN and alkylthio;
$R^6$ is independently selected from the group consisting of lower alkyl and lower cycloalkyl; and
$R^7$, $R^{7a}$ and $R^{7b}$ are independently selected from the group consisting of hydrogen, lower alkyl and lower cycloalkyl, wherein two $R^7$ groups and the atom to which they are attached may optionally form a heterocyclyl of 4 to 7 atoms;
$R^8$, $R^9$, and $R^{9a}$, $R^{10}$ and $R^{11}$ are independently selected from the group consisting of hydrogen and alkyl;
n is 2; or
a pharmaceutically acceptable salt thereof; a stereoisomer thereof; or a prodrug ester thereof.

2. The compound according to claim 1, wherein Q is $-(CR^8R^9)_n-$.

3. The compound according to claim 1, wherein W is selected from the group consisting of a direct bond and $-O-$.

4. The compound according to claim 1, wherein D is selected from the group consisting of a direct bond and alkyl.

5. The compound according to claim 1, wherein $R^{1b}$ is phenyl.

6. The compound according to claim 5, wherein the $R^{1b}$ phenyl is substituted with one $R^4$ substitutent at the para-position.

7. The compound according to claim 6, wherein the $R^4$ substitutent is selected from the group consisting of halo and polyfluoroalkyl.

8. The compound according to claim 1 wherein A is phenyl.

9. The compound according to claim 1, wherein $R^3$ is selected from the group consisting of hydrogen, alkoxy, halo and alkyl.

10. The compound as defined in claim 1 wherein $R^2$ is heteocyclyl, OH, hydroxyalkyl,

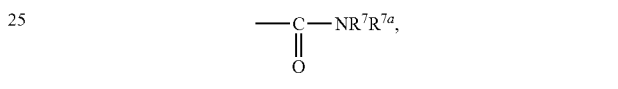

$-NR^7R^{7a}$, or heteroaryl.

11. The compound as defined in claim 1 wherein $R^{1a}$ is H or halo, $R^{1b}$ is

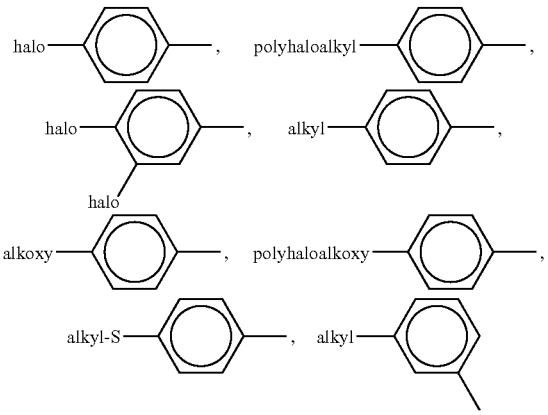

and $R^{1c}$ is H or halo.

12. The compound as defined in claim 1 wherein Q is CH$_2$CH$_2$.

13. The compound as defined in claim 1 wherein A is

14. The compound as defined in claim 9 wherein $R^3$ is H or alkoxy.

15. The compound as defined in claim 4 wherein D is CH$_2$, CH$_2$CH$_2$, CH$_2$CH$_2$CH$_2$,

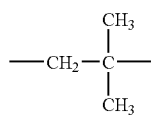
or a bond.
16. The compound a defined in claim 10 wherein $R^2$ is
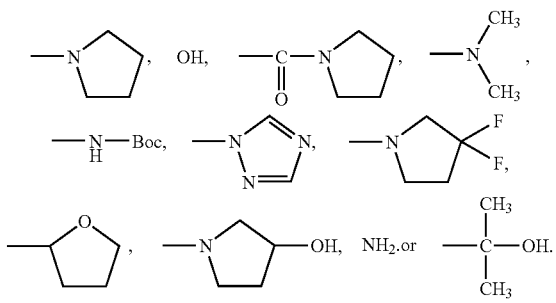
17. The compound as defined in claim 1 wherein $R^{1a}$ is H or Br or Cl;
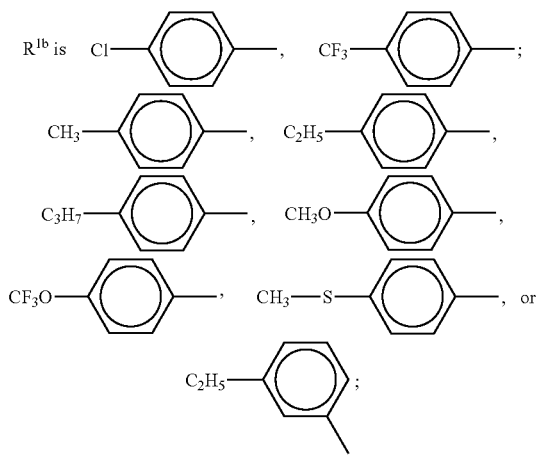
$R^{1c}$ is H or Br or Cl;
Q is $CH_2CH_2$;
$R^3$ is H or $CH_3O$;
W is a bond or O;
D is —$CH_2CH_2CH_2$—, —$CH_2CH_2$—,
—$CH_2$—$C(CH_3)_2$—, $CH_2$ or a bond;
$R^2$ is
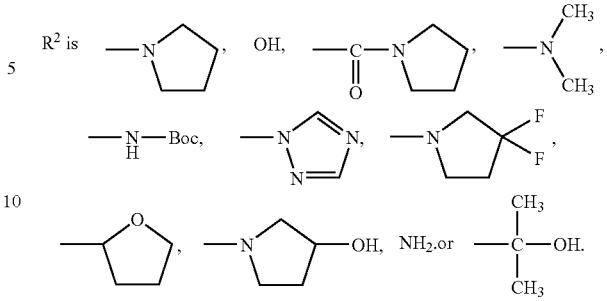
18. The compound according to claim 1, wherein the compound is selected from the group consisting of
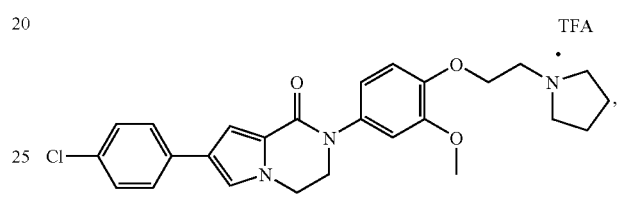
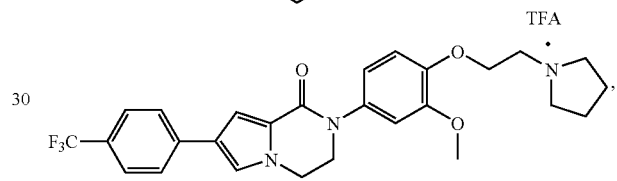
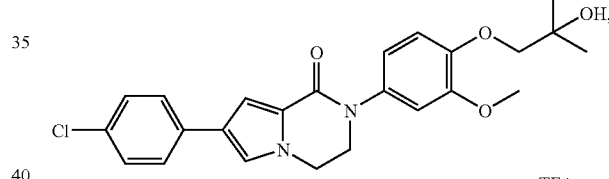
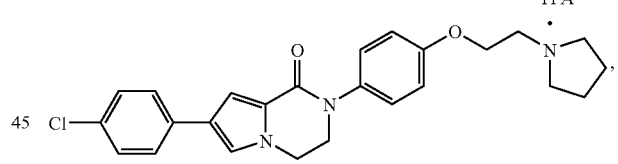
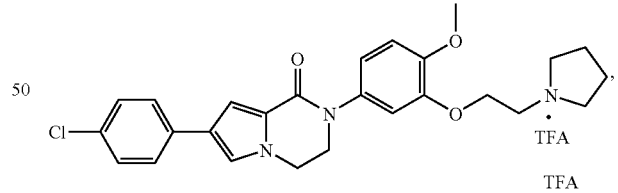
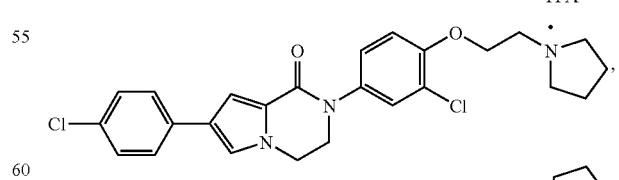
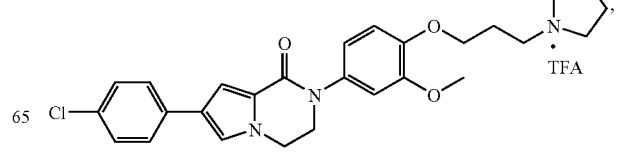

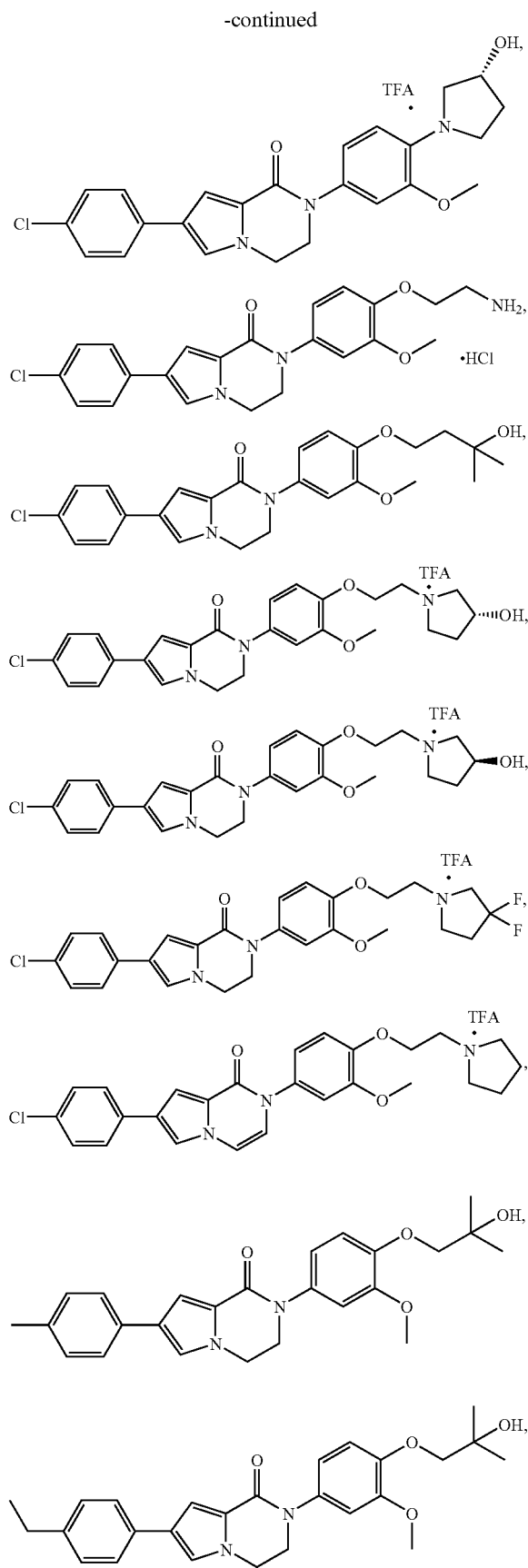

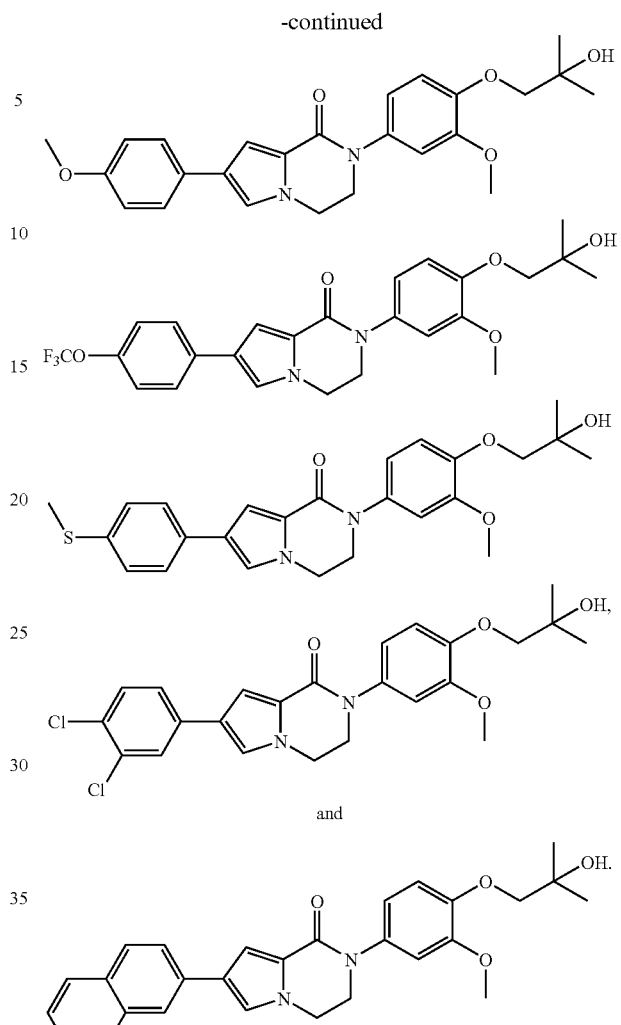

and

19. A pharmaceutical composition, comprising:
at least one compound according to claim 1; and
at least one pharmaceutically acceptable carrier or diluent.

20. The pharmaceutical composition according to claim 19, further comprising:
at least one additional therapeutic agent.

21. A pharmaceutical combination, comprising:
at least one compound according to claim 1; and
at least one additional therapeutic agent.

22. The pharmaceutical combination according to claim 21, wherein the additional therapeutic agent is administered before, concurrent or after said compound.

23. The combination as defined in claim 22 wherein the additional therapeutic agent is an acetyl-cholinesterase inhibitor, a muscarinic receptor-1 agonist, a nicotinic agonist, a glutamic acid receptor (AMPA and NMDA) modulator, a nootropic agent, an agent for Alzheimer's disease, an agent for treatment of Parkinson's disease.

24. The combination as defined in claim 22 wherein the additional therapeutic agent is an anti-obesity agent; anti-diabetic agent, appetite suppressant; cholesterol/lipid- owering agent, HDL-raising agent, cognition enhancing agent, an agent used to treat neurodegeneration, an agent used to treat respiratory conditions, an agent used to treat bowel disorders, an anti-inflammatory agent; anti-anxiety agent; an anti-depressant; an anti-hypertensive agent; a cardiac glycoside; or an anti-tumor agent.

25. The combination as defined in claim 24 wherein the anti-obesity agent is a melanocortin receptor (MC4R) agonist, a cannabinoid receptor modulator, a growth hormone secretagogue receptor (GHSR) antagonist, a galanin receptor modulator, an orexin antagonist, a CCK agonist, a GLP-1 agonist, a Pre-proglucagon-derived peptides; an NPY1 or NPY5 antagonsist, an NPY2 or NPY4 modulator, a corticotropin releasing factor agonist, a histamine receptor-3 (H3) modulator, an aP2 inhibitor, a PRAR gamma modulator, a PPAR delta modulator, an acetyl-CoA carboxylase (ACC) inhibitor, an 11-β-HSD-1 inhibitor, an adinopectin receptor modulator; a beta 3 adrenergic agonist, a thyroid receptor beta modulator, a lipase inhibitor, a serotonin receptor agonist, a monoamine reuptake inhibitor or releasing agent, an anorectic agnet, a CNTF (ciliary neurotrophic factor), a BDNF (brain-derived neurotrophic factor), a leptin and leptin receptor modulator, or a cannabinoid-1 receptor antagonist.

26. The combination as defined in claim 22 wherein the antidiabetic agent is an insulin secretagogue or insulin sensitizer, which is a biguanide, a sulfonyl urea, a glucosidase inhibitor, an aldose reductase inhibitor, a PPAR γ agonist, a PPAR α agonist, a PPAR δ antagonist or agonist, a PPAR α/γ dual agonist, an 11-β-HSD-1 inhibitor, a dipeptidyl peptidase IV (DP4) inhibitor, a SGLT2 inhibitor, a glycogen phosphorylase inhibitor, a meglitinide, a glucagon-like peptide-1 (GLP-1), a GLP-1 agonist, and/or a PTP-1B inhibitor (protein tyrosine phosphatase-1B inhibitor).

27. The combination as defined in claim 22 wherein the additional therapeutic agent is an anti-hyperlipidemia agent, or agent used to treat arteriosclerosis, which is an HMG CoA reductase inhibitor, a squalene synthetase inhibitor, a fibric acid derivative, aspirin, a bile acid sequestrant, an ACAT inhibitor, an upregulator of LDL receptor activity, a cholesterol absorption inhibitor, a cholesteryl transfer protein (CETP) inhibitor, an ileal Na+/bile acid cotransporter inhibitor, a phytoestrogen, a beta-lactam cholesterol absorption inhibitor, an HDL upregulator, a PPAR α-agonist and/or an FXR agonist; an LDL catabolism promoter such, a sodium-proton exchange inhibitor, an LDL-receptor inducer or a steroidal glycoside, an anti-oxidant, or an antihomocysteine agent, isoniazid, an HMG-CoA synthase inhibitor, or a lanosterol demethylase inhibitor, a PPAR δ agonist, or a sterol regulating element binding protein-l (SREBP-1).

28. The combination as defined in claim 22 wherein the additional therapeutic agent is an anti-hypertensive agent, which is a beta adrenergic blocker, a calcium channel blocker (L-type and/or T-type), a diuretic, a renin inhibitor, an ACE inhibitor, an AT-1 receptor antagonist, an ET receptor antagonist, a Dual ET/AII antagonist, a neutral endopeptidase (NEP) inhibitor, a vasopeptidase inhibitor (dual NEP-ACE inhibitor) or a nitrate;

an MCHR1 antagonist for treating a sleep disorder which is a melatonin analog, a melatonin receptor antagonist, an ML 1 B agonist, a GABA receptor modulator, an NMDA receptor modulator, a histamine-3 (H3) receptor modulator, a dopamine agonist or an orexin receptor modulator; an agent for treating substance abuse or, addictive disorders which is a cannabinoid receptor modulator, a selective serotonin reuptake inhibitor (SSRI), methadone, buprenorphine, nicotine or bupropion;

an MCHR1 antagonist to reduce anxiety or depression, anti-anxiety agents or antidepressants, which is a benzodiazepine, a 5HT1A receptor agonist, or a corticotropin eleasing factor (CRF) antagonist; or a norepinephrine reuptake inhibitor (tertiary and secondary amine tricyclics), a selective serotonin reuptake inhibitor (SSRI), a monoamine oxidase inhibitor (MAOI), a reversible inhibitor of monoamine oxidase (RIMA), a serotonin and norepinephrine reuptake inhibitor (SNRI), a corticotropin releasing factor (CRF) receptor antagonist, an alpha-adrenoreceptor antagonist, an atypical antidepressant, or an antipsychotic drug for treatment of psychosis or mania.

* * * * *

UNITED STATES PATENT AND TRADEMARK OFFICE
CERTIFICATE OF CORRECTION

PATENT NO. : 7,553,836 B2
APPLICATION NO. : 11/671150
DATED : June 30, 2009
INVENTOR(S) : Guohua Zhao It is certified that error appears in the above-identified patent and that said Letters Patent is hereby corrected as shown below:

Column 58
Line 64-65, "lipid- owering" should read -- lipid-lowering --.

Column 59
Line 12, "PRAR" should read -- PPAR --.

Column 60
Line 7, "protein-1" should read -- protein-I --; and
Line 28, "eleasing" should read -- releasing --.

Signed and Sealed this

Fourteenth Day of September, 2010

David J. Kappos
*Director of the United States Patent and Trademark Office*